US008193192B2

(12) United States Patent
Kremoser et al.

(10) Patent No.: US 8,193,192 B2
(45) Date of Patent: Jun. 5, 2012

(54) HETEROCYCLIC FXR BINDING COMPOUNDS

(75) Inventors: Claus Kremoser, Heidelberg (DE); Ulrich Deuschle, Worms (DE); Ulrich Abel, Heidelberg (DE); Andreas Schulz, Heidelberg (DE)

(73) Assignee: Phenex Pharmaceuticals AG, Ludwigshafen (DE)

( * ) Notice: Subject to any disclaimer, the term of this patent is extended or adjusted under 35 U.S.C. 154(b) by 512 days.

(21) Appl. No.: 12/377,307

(22) PCT Filed: Aug. 29, 2007

(86) PCT No.: PCT/EP2007/007556
§ 371 (c)(1),
(2), (4) Date: Mar. 30, 2009

(87) PCT Pub. No.: WO2008/025539
PCT Pub. Date: Mar. 6, 2008

(65) Prior Publication Data
US 2010/0210660 A1    Aug. 19, 2010

Related U.S. Application Data

(60) Provisional application No. 60/840,912, filed on Aug. 29, 2006.

(30) Foreign Application Priority Data

Aug. 29, 2006  (EP) .................................. 06018024

(51) Int. Cl.
| A61K 31/50 | (2006.01) |
| A61K 31/501 | (2006.01) |
| A61K 31/497 | (2006.01) |
| C07D 413/00 | (2006.01) |
| C07D 401/00 | (2006.01) |
| C07D 403/00 | (2006.01) |
| C07D 405/00 | (2006.01) |
| C07D 409/00 | (2006.01) |

(52) U.S. Cl. ........... 514/252.01; 514/252.04; 514/252.1; 514/252.12; 546/272.1; 544/238

(58) Field of Classification Search ............. 514/252.01, 514/252.04, 252.12; 546/272.1; 544/238
See application file for complete search history.

(56) References Cited

U.S. PATENT DOCUMENTS
| 5,883,105 A | 3/1999 | Anthony |
| 6,187,797 B1 | 2/2001 | Pruitt et al. |
| 2009/0093524 A1 | 4/2009 | Bell et al. |

FOREIGN PATENT DOCUMENTS
| EP | 0573883 A1 | 12/1993 |
| WO | 9857937 A2 | 12/1998 |
| WO | 9924404 A1 | 5/1999 |
| WO | 03015771 A1 | 2/2003 |
| WO | 2004048349 A1 | 6/2004 |
| WO | 2005113494 A2 | 12/2005 |

OTHER PUBLICATIONS

Vippagunta et al. Advanced Drug Delivery Reviews, 2001, vol. 48, pp. 3-26.*
Pellicciari et al., "Potential therapeutic applications of farnesoid X receptor (FXR) modulators," Expert Opinion on Therapeutic Patents 2006, vol. 16, No. 3, 2006 (pp. 333-341).
European Search Report for corresponding European Patent Application No. EP 06 01 8024 dated Jan. 31, 2007 (2 pages).
International Preliminary Report on Patentability for corresponding International Patent Application No. PCT/EP2007/007556 dated Nov. 21, 2008 (17 pages).
Office Action dated Nov. 15, 2011, 12 pages, U.S. Appl. No. 12/376,482, applicant(s): Kremoser et al.
Patani et al., "Bioisterism: A Rational Approach in Drug Design," Chemical Reviews 1996, 96, 3147-3176.
West, Anthony R., Solid State Chemistry and its Applications, Wiley, New York, 1988, pp. 358 and 365.
Office Action dated Jun. 27, 2011, 18 pages, U.S. Appl. No. 12/376,482, applicant(s): Kremoser et al.

* cited by examiner

*Primary Examiner* — Samira Jean-Louis
(74) *Attorney, Agent, or Firm* — Kilyk & Bowersox, P.L.L.C.

(57) ABSTRACT

The present invention relates to compounds which bind to the NR1H4 receptor (FXR) and act as agonists or partial agonists of the NR1H4 receptor (FXR). The invention further relates to the use of the compounds for the preparation of a medicament for the treatment of diseases and/or conditions through binding of said nuclear receptor by said compounds, and to a process for the synthesis of said compounds.

40 Claims, 1 Drawing Sheet

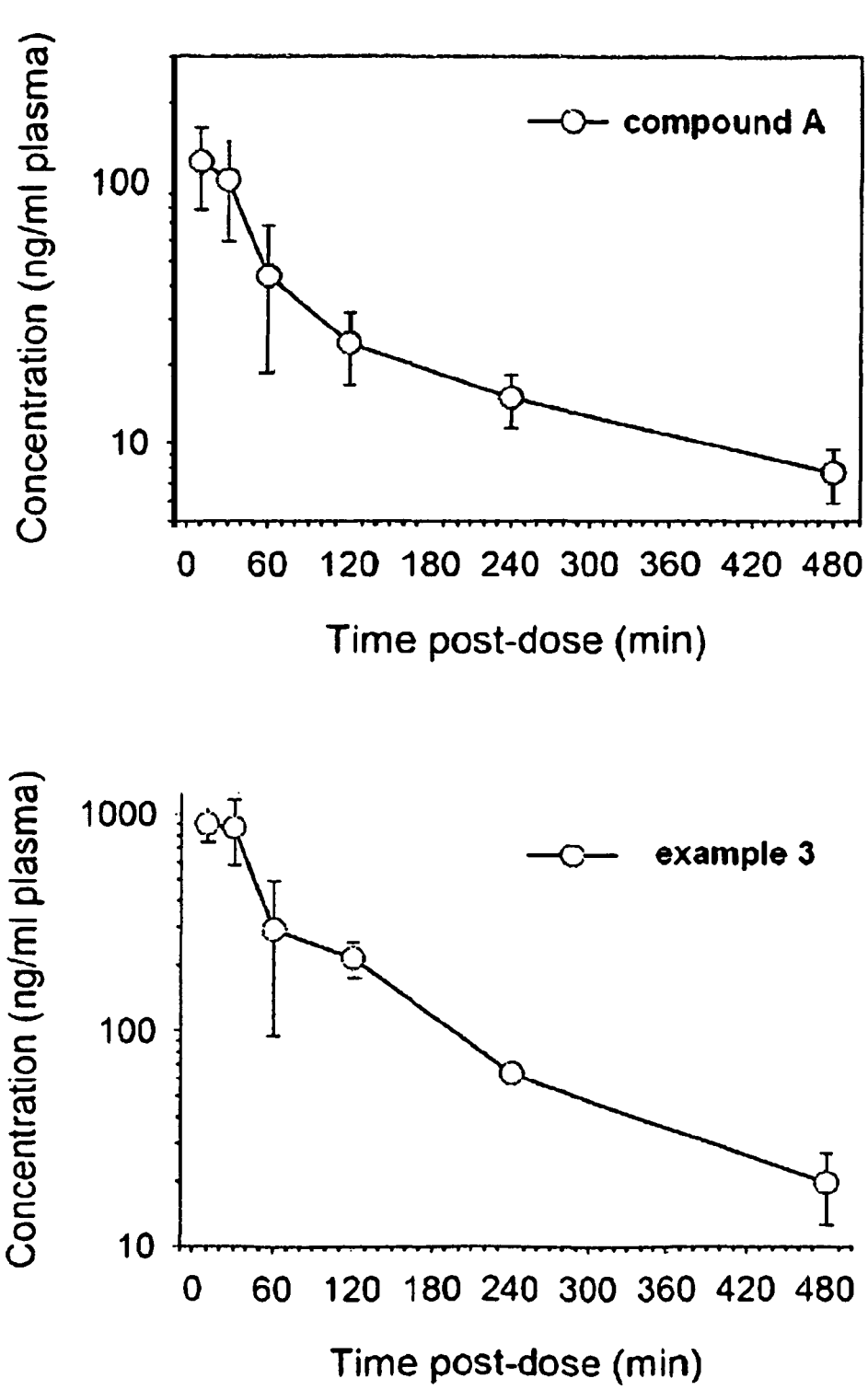

HETEROCYCLIC FXR BINDING COMPOUNDS

This application is a National Stage Application of International Application No. PCT/EP2007/007556, filed Aug. 29, 2007, which claims priority from European Patent Application No. 06018024.7, filed Aug. 29, 2006, and from U.S. Provisional Patent Application No. 60/840,912, filed Aug. 29, 2006.

The present invention relates to compounds which bind to the NR1H4 receptor (FXR) and act as agonists or partial agonists of the NR1H4 receptor (FXR). The invention further relates to the use of the compounds for the preparation of a medicament for the treatment of diseases and/or conditions through binding of said nuclear receptor by said compounds, and to a process for the synthesis of said compounds.

Multicellular organisms are dependent on advanced mechanisms of information transfer between cells and body compartments. The information that is transmitted can be highly complex and can result in the alteration of genetic programs involved in cellular differentiation, proliferation, or reproduction. The signals, or hormones, are often low molecular weight molecules, such as peptides, fatty acid, or cholesterol derivatives.

Many of these signals produce their effects by ultimately changing the transcription of specific genes. One well-studied group of proteins that mediate a cell's response to a variety of signals is the family of transcription factors known as nuclear receptors, hereinafter referred to often as "NR". Members of this group include receptors for steroid hormones, vitamin D, ecdysone, cis and trans retinoic acid, thyroid hormone, bile acids, cholesterol-derivatives, fatty acids (and other peroxisomal proliferators), as well as so-called orphan receptors, proteins that are structurally similar to other members of this group, but for which no ligands are known. Orphan receptors may be indicative of unknown signalling pathways in the cell or may be nuclear receptors that function without ligand activation. The activation of transcription by some of these orphan receptors may occur in the absence of an exogenous ligand and/or through signal transduction pathways originating from the cell surface (D. Mangelsdorf et al. "The nuclear receptor superfamily: the second decade", Cell 1995, 83(6), 835-839; R Evans "The nuclear receptor superfamily: a rosetta stone for physiology" Mol. Endocrinol. 2005, 19(6), 1429-1438).

In general, three functional domains have been defined in NRs. An amino terminal domain is believed to have some regulatory function. A DNA-binding domain hereinafter referred to as "DBD" usually comprises two zinc finger elements and recognizes a specific Hormone Responsive Element hereinafter referred to as "HRE" within the promoters of responsive genes. Specific amino acid residues in the "DBD" have been shown to confer DNA sequence binding specificity (M. Schena "Mammalian glucocorticoid receptor derivatives enhance transcription in yeast", Science 1988, 241(4868), 965-967). A ligand-binding-domain hereinafter referred to as "LBD" is at the carboxy-terminal region of known NRs.

In the absence of hormone, the LBD appears to interfere with the interaction of the DBD with its HRE. Hormone binding seems to result in a conformational change in the NR and thus opens this interference (A. Brzozowski et al. "Molecular basis of agonism and antagonism in the oestrogen receptor" Nature 1997, 389(6652), 753-758). A NR without the LBD constitutively activates transcription but at a low level.

Coactivators or transcriptional activators are proposed to bridge between sequence specific transcription factors, the basal transcription machinery and in addition to influence the chromatin structure of a target cell. Several proteins like SRC-1, ACTR, and Grip1 interact with NRs in a ligand enhanced manner (D. Heery et al. "A signature motif in transcriptional co-activators mediates binding to nuclear receptors" Nature 1997, 387(6634), 733-6.; T. Heinzel et al. "A complex containing N—CoR, mSin3 and histone deacetylase mediates transcriptional repression" Nature 1997, 387(6628), 16-17; K. Nettles, G. Greene "Ligand control of coregulator recruitment to nuclear receptors" Annu. Rev. Physiol. 2005, 67, 309-33).

Nuclear receptor modulators like steroid hormones affect the growth and function of specific cells by binding to intracellular receptors and forming nuclear receptor-ligand complexes. Nuclear receptor-hormone complexes then interact with a hormone response element (HRE) in the control region of specific genes and alter specific gene expression (A. Aranda, A. Pascual "Nuclear hormone receptors and gene expression" Physiol. Rev. 2001, 81(3), 1269-1304).

The Farnesoid X Receptor alpha (hereinafter also often referred to as NR1H4 when referring to the human receptor) is a prototypical type 2 nuclear receptor which activates genes upon binding to promoter region of target genes in a heterodimeric fashion with Retinoid X Receptor (B. Forman et al. "Identification of a nuclear receptor that is activated by farnesol metabolites" Cell 1995, 81(5), 687-693). The relevant physiological ligands of NR1H4 are bile acids (D. Parks et al. "Bile acids: natural ligands for an orphan nuclear receptor" Science 1999, 284(5418), 1365-1368; M. Makishima et al. "Identification of a nuclear receptor for bile acids" Science 1999, 284(5418), 1362-1365). The most potent one is chenodeoxycholic acid (CDCA), which regulates the expression of several genes that participate in bile acid homeostasis.

Farnesol and derivatives, together called farnesoids, are originally described to activate the rat orthologue at high concentration but they do not activate the human or mouse receptor. FXR is expressed in the liver, small intestine, colon, ovary, adrenal gland and kidney. Beyond controlling intracellular gene expression, FXR seems to be also involved in paracrine and endocrine signaling (J. Holt et al. "Definition of a novel growth factor-dependent signal cascade for the suppression of bile add biosynthesis" Genes Dev. 2003, 11(13), 1581-91; T. Inagaki et al. "Fibroblast growth factor 15 functions as an enterohepatic signal to regulate bile add homeostasis" Cell Metab. 2005, 2(4), 217-225).

There is one publication which proposes a direct impact of FXR activation on the survival of infectious organisms such as bacteria or protozoic parasites via the upregulation of the lysosomal fate/survival factor Taco-2 in macrophages (P. Anand et al. "Downregulation of TACO gene transcription restricts mycobacterial entry/survival within human macrophages" FEMS Microbiol. Lett. 2005, 250(1), 137-144). This might pave the way for further studies that assess the suitability of FXR to act as drug target for the treatment of intracellular bacterial or parasitic infections such as Tuberculosis, Lepra, Leishmaniosis or Trypanosomiasis, e.g. Chagas Disease.

Small molecule compounds which act as FXR modulators have been disclosed in the following publications: WO 2004/048349, WO 2003/015771 and WO 2000/037077. Further small molecule FXR modulators have been recently reviewed (R. C. Buijsman et al. "Non-Steroidal Steroid Receptor Modulators" Curr. Med. Chem. 2005, 12, 1017-1075).

Many of the failures of drug candidates in development programs are attributed to their undesirable pharmacokinetic properties, such as too long or too short $t_{1/2}$, poor absorption, and extensive first-pass metabolism. In a survey, it was reported that of 319 new drug candidates investigated in humans, 77 (40%) of the 198 candidates were withdrawn due to serious pharmacokinetic problems (R. Prentis et al, "Pharmaceutical innovation by seven UK-owned pharmaceutical companies (1964-1985)" Br. J. Clin. Pharmacol. 1988, 25, 387-396). This high failure rate illustrates the importance of pharmacokinetics in drug discovery and development. To ensure the success of a drug's development, it is essential that a drug candidate has good bioavailability and a desirable $t_{1/2}$. Therefore, an accurate estimate of the pharmacokinetic data and a good understanding of the factors that affect the pharmacokinetics will guide drug design (J. Lin, A. Lu "Role of pharmacokinetics and Metabolism in Drug Discovery and Development" Pharmacol. Rev. 1997, 49(4), 404-449). Chemically modifiable factors that influence drug absorption and disposition are discussed as follows.

Some relevant physicochemical and ADME parameters include but are not limited to: aqueous solubility, logD, PAMPA permeability, Caco-2 permeability, plasma protein binding, microsomal stability and hepatocyte stability.

Poor aqueous solubility can limit the absorption of compounds from the gastrointestinal (GI) tract, resulting in reduced oral bioavailability. It may also necessitate novel formulation strategies and hence increase cost and delays. Moreover, compound solubility can affect other in vitro assays. Poor aqueous solubility is an undesired characteristic and it is the largest physicochemical problem hindering oral drug activity (C. A. Lipinski "Drug-like properties and the causes of poor solubility and poor permeability", J. Pharmacol. Toxicol. Methods 2000, 44, 235-249).

Lipophilicity is a key determinant of the pharmacokinetic behaviour of drugs. It can influence distribution into tissues, absorption and the binding characteristics of a drug, as well as being an important factor in determining the solubility of a compound. LogD (distribution coefficient) is used as a measure of lipophilicity. One of the most common methods for determining this parameter is by measuring the partition of a compound between an organic solvent (typically octanol) and aqueous buffer. An optimal range for lipophilicity tends to be if the compound has a logD value between 0 and 3. Typically, these compounds have a good balance between solubility and permeability and this range tends to be optimal for oral absorption and cell membrane permeation. Hydrophilic compounds (logD<0) typically are highly soluble but exhibit low permeability across the gastrointestinal tract or blood brain barrier. Highly lipophilic compounds (logD>5) exhibit problems with metabolic instability, high plasma protein binding and low solubility which leads to variable and poor oral absorption (L. Di, E. Kerns "Profiling drug-like properties in discovery research" Curr. Opin. Chem. Biol. 2003, 7, 402-408).

Drug permeability through cell monolayers or artificial membranes correlates well with intestinal permeability and oral bioavailability. Drugs with low membrane permeability, i.e. low lipophilicity, are generally absorbed slowly from solution in the stomach and small intestine. Knowing the rate and extent of absorption across the intestinal tract is critical if a drug is to be orally delivered. Drug permeability cannot be accurately predicted by physicochemical factors alone because there are many drug transport pathways. A generally accepted human cell-based model, human colon adenocarcinoma cell line (Caco-2), helps to predict intestinal permeability (A. M. Marino et al. "Validation of the 96-well Caco-2 cell culture model for high-throughput permeability and assessment of discovery compounds", Int. J. Pharmaceutics 2005, 297; 235-241). This assay is commonly employed during early discovery, especially in lead optimisation. A newer in vitro model, known as the parallel artificial membrane permeability assay (PAMPA) ranks compounds on their passive diffusion rates alone. PAMPA is increasingly used as the first-line permeability screen during lead profiling (F. Wohnsland, B. Faller "High-throughput Permeability pH Profile and High-throughput Alkane/Water Log P With Artificial Membranes", J. Med. Chem. 2001, 44, 923-930).

Plasma protein binding (PPB) can significantly affect the therapeutic action of a drug. It determines the extent and duration of action because only unbound drug is thought to be available for passive diffusion to extravascular space or tissue sites where therapeutic effects occur. The level of PPB is important for predicting the pharmacokinetic profile of a drug and determining appropriate oral dosing. In vivo dose levels can be estimated from the determined fraction of unbound drug (fu); an increase in dose may be necessary if a drug is highly bound to plasma (Y. Kwon "Handbook of essential pharmacokinetics, pharmacodynamics and drug metabolism for industrial scientists" Springer Verlag 2001).

In vitro models to predict compound metabolism have become accepted adjuncts to animal testing. Early drug metabolism models help predict the metabolic stability of a compound and there are several approaches to doing this. The enzyme sources in these studies are rat or human derived systems that consist of liver microsomes and hepatocytes. Microsomes contain the full complement of phase I oxidative enzymes but do not have an intact cell membrane. Moreover, microsomes require the addition of a co-factor to the incubation. Hepatocytes are more representative of the in vitro situation because they contain a cell membrane and do not require additional co-factors. Hepatocytes contain enzymes for both phase I (oxidation, reduction and/or hydrolysis of test compound) and phase II (conjugation of test compounds or metabolites from phase I) metabolism. The microsomal stability screen is often used as a primary screen early in the drug discovery process. The hepatocyte stability assay is used as a secondary screen for the more favourable compounds discovered from the primary screen (T. Iwatsubo et. al. "Prediction of in vivo drug metabolism in the human liver from in vitro metabolism data", Pharm. Ther. 1997, 73, 147-171).

In summary, favourable physicochemical and in vitro ADME parameters are prerequisite for a favourable pharmacokinetic (PK) profile of a drug. Obtaining early stage PK data evaluation of new chemical entities is a prerequisite for successful animal pharmacology and toxicology studies. Quantitative measures of drug exposure are key components needed for the sound interpretation of preclinical efficacy studies. PK data can also help in the design or species selection of preclinical toxicology studies. Pharmacokinetic studies are part of the regulatory drug development requirements and have also started to become an integral part of the early drug discovery process.

It is the object of the present invention to provide novel compounds that are agonists or partial agonists of FXR exhibiting physicochemical, in vitro and/or in vivo ADME (absorption, distribution, metabolism and excretion) properties superior to known agonists of FXR and/or superior pharmacokinetics in viva. Physicochemical and ADME properties affect drug pharmacokinetics and can be assessed by in vitro methods.

Unexpectedly, we found that FXR modulating compounds described herein show improved physicochemical and/or ADME parameters in vitro resulting in advanced pharmacokinetic properties, i.e. a superior bioavailability and a favourable half life in viva in comparison to the compounds disclosed in the prior art.

As a result, the present invention relates to compounds according to the general formula (I) which bind to the NR1H4 receptor (FXR) and act as agonists or partial agonists of the NR1H4 receptor (FXR). The invention further relates to the use of said compounds for the preparation of medicaments for the treatment of diseases and/or conditions through binding of said nuclear receptor by said compounds. The invention further also describes a method for the synthesis of said compounds. The compounds of the present invention show improved physicochemical and/or ADME parameters in vitro finally resulting in advanced pharmacokinetic properties in vivo.

BRIEF DESCRIPTION OF THE DRAWINGS

FIG. 1: Graphical depiction of pharmacokinetic data of compound A compared to example 3. Compound plasma concentrations (logarithmic scale) are plottet against sampling timepoints. Conditions: C57BL/6 mice, oral cassette dosing, 5 mg/Kg in 10% HPBCD/20 mM phosphate buffer.

The compounds of the present invention are defined by formula (I):

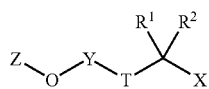

(I)

including enantiomers, diastereomers, tautomers, solvates and pharmaceutically acceptable salts thereof, wherein $R^1$ and $R^2$ are independently from each other selected from hydrogen, fluorine, cyano, nitro, azido, $NR^5R^6$, $OR^5$, $SR^5$, $C_1$-$C_6$ alkyl, $C_2$-$C_6$ alkenyl, $C_2$-$C_6$ alkynyl, $C_3$-$C_6$ cycloalkyl; or $R^1$ and $R^2$ are together =O or =S; or $R^1$ and $R^2$ may together form a 3-6-membered carbocyclic or heterocyclic ring which each can be unsaturated or saturated, wherein each alkyl, alkenyl, alkynyl, cycloalkyl group, carbocyclic or heterocyclic ring is unsubstituted or substituted with one to five substituents $R^{11}$;

$R^5$ and $R^6$ are independently from each other selected from hydrogen, $C_1$-$C_6$-alkyl and $C_3$-$C_6$-cycloalkyl; or $R^5$ and $R^6$ together may form a 3-6-membered saturated heterocyclic ring, wherein the alkyl, cycloalkyl and heterocyclic group is unsubstituted or substituted with one to five substituents $R^{11}$;

X is

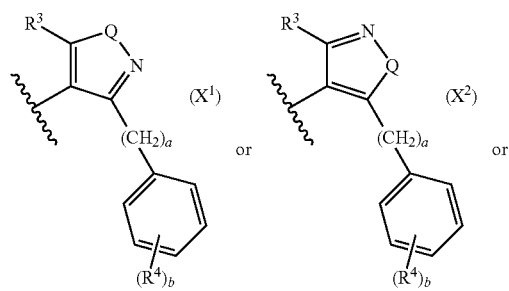

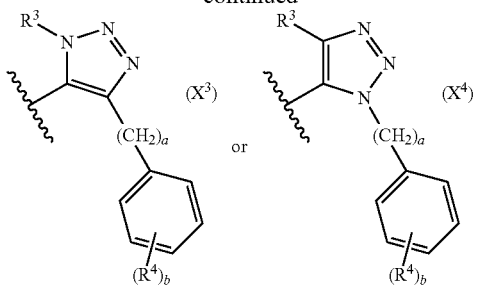

in each $X^1$, $X^2$, $X^4$
$R^3$ is hydrogen, halogen, cyano, nitro, azido, $C_1$-$C_6$ alkyl, $C_2$-$C_6$ alkenyl, $C_2$-$C_6$ alkynyl, $C_3$-$C_6$ cycloalkyl, heterocyclyl, aryl, heteroaryl, —$NR^{19}R^{20}$, $NR^{19}S(O)_mR^{20}$, $NR^{19}C(O)OR^{20}$, $NR^{19}C(O)R^{20}$, $NR^{19}C(O)NR^{19}R^{20}$, $OR^{19}$, $OC(O)R^{19}$, $S(O)_iR^{19}$, $SO_2NR^{19}C(O)R^{20}$, $S(O)_mNR^{19}R^{20}$, $C(O)R^{19}$, $C(O)OR^{20}$, $C(O)NR^{19}R^{20}$, $C(NR^{19})NR^{19}R^{20}$, wherein each alkyl, alkenyl, alkynyl, cycloalkyl heterocyclyl, aryl or heteroaryl is unsubstituted or substituted with one to five substituents $R^{11}$;

in each $X^3$
$R^3$ is hydrogen, $C_1$-$C_6$ alkyl, $C_2$-$C_6$ alkenyl, $C_2$-$C_6$ alkynyl, $C_3$-$C_6$ cycloalkyl, heterocyclyl, aryl, heteroaryl, $SO_2R^{19}$, $C(O)R^{19}$, $C(O)OR^{19}$, $C(O)NR^{19}R^{20}$, wherein each alkyl, alkenyl, alkynyl, cycloalkyl, heterocyclyl, aryl or heteroaryl is unsubstituted or substituted with one to five substituents $R^{11}$;

$R^{19}$ and $R^{20}$ are independently from each other selected from hydrogen, $C_1$-$C_6$-alkyl, $C_2$-$C_6$-alkenyl, $C_2$-$C_6$ alkynyl, $C_3$-$C_6$-cycloalkyl, or $R^{19}$ and $R^{20}$ together may form a 3-7-membered heterocyclic or heteroaromatic ring, and wherein the $C_1$-$C_6$-alkyl, $C_{2-6}$-alkenyl, $C_3$-$C_6$-cycloalkyl, heterocyclyl and heteroaryl groups are unsubstituted or substituted with one to five substituents $R^{11}$;

$R^4$ is independently selected from hydrogen, halogen, cyano, nitro, azido, $C_1$-$C_6$ alkyl, $C_2$-$C_6$ alkenyl, $C_2$-$C_6$ alkynyl, $C_3$-$C_6$ cycloalkyl, heterocyclyl, aryl, heteroaryl, $NR^{15}R^{16}$, $NR^{15}SO_2R^{16}$, $NR^{15}C(O)OR^{16}$, $NR^{15}C(O)R^{16}$, $NR^{15}C(O)NR^{15}R^{16}$, $NR^{15}C(NCN)NR^{15}R^{16}$, $OR^{15}$, $OC(O)R^{15}$, $S(O)_iR^{15}$, $SO_2NR^{15}C(O)R^{16}$, $S(O)_mNR^{15}R^{16}$, $SC(O)R^{15}$, $C(O)R^{15}$, $C(O)OR^{15}$, $C(O)NR^{15}R^{16}$, $C(O)NHOR^{15}$, $C(O)SR^{15}$, $C(NR^{15})NR^{15}R^{16}$, wherein each alkyl, alkenyl, alkynyl, cycloalkyl, heterocyclyl, aryl or heteroaryl is unsubstituted or substituted with one to five substituents $R^{11}$;

and further two substituents $R^4$ can be taken together with the atom to which they attach to form a 4-7 membered carbocyclic, aryl, heteroaryl or heterocyclic ring, each of which is substituted or unsubstituted with one to five substituents $R^{11}$;

$R^{15}$ and $R^{16}$ are independently from each other selected from hydrogen, $C_1$-$C_6$-alkyl, $C_2$-$C_6$-alkenyl, $C_2$-$C_6$ alkynyl, $C_3$-$C_6$-cycloalkyl; or $R^{15}$ and $R^{16}$ together may form a 3-7-membered heterocyclic or heteroaromatic ring, and wherein the $C_1$-$C_6$-alkyl, $C_2$-$C_6$-alkenyl, $C_3$-$C_6$-cycloalkyl, heterocyclyl and heteroaryl groups are unsubstituted or substituted with one to five substituents $R^{11}$;

$R^{11}$ is independently selected from hydrogen, halogen, cyano, nitro, azido, =O, =S, $C_1$-$C_6$ alkyl, $C_2$-$C_6$ alkenyl, $C_2$-$C_6$ alkynyl, $C_3$-$C_6$ cycloalkyl, heterocyclyl, aryl, heteroaryl, $NR^{12}R^{13}$, $NR^{12}S(O)_mR^{13}$, $NR^{12}C(O)OR^{13}$, $NR^{12}C(O)R^{13}$, $NR^{12}C(O)NR^{12}R^{13}$, $NR^{12}C(NCN)NR^{12}R^{13}$, =$NOR^{12}$, —$OR^{12}$, $OC(O)R^{12}$, $S(O)_iR^{12}$, $SO_2NR^{12}C(O)R^{13}$, $S(O)_mNR^{12}R^{13}$, $SC(O)R^{12}$, $C(O)R^{12}$, $C(O)OR^{12}$, $C(O)SR^{12}$, $C(O)NR^{12}R^{13}$, $C(O)NOR^{12}$, and $C(NR^{12})NR^{12}R^{13}$;

$R^{12}$ and $R^{13}$ are independently from each other selected from hydrogen, $C_1$-$C_6$ alkyl or $C_3$-$C_6$ cycloalkyl, wherein each alkyl or cycloalkyl may be unsubstituted or substituted with one to five fluorines and/or one or two substituents selected from OH, $OCH_3$, $OCH_2F$, $OCHF_2$, $OCF_3$, =O, $SCF_3$, $NH_2$, $NHCH_3$ and $N(CH_3)_2$; or $R^{12}$ and $R^{13}$ can be taken together with the atom to which they are attached to form a 4 to 6 membered carbocyclic, heteroaryl or heterocyclic ring, each of which may be unsubstituted or substituted with one to five fluorines and/or one or two substituents selected from OH, $OCH_3$, —$OCH_2F$, $OCHF_2$, $OCF_3$, =O, $SCF_3$, $NH_2$, $NHCH_3$ and $N(CH_3)_2$;

Q is O or $NR^7$;

$R^7$ is hydrogen, $C_1$-$C_3$-alkyl, or $C_3$-$C_5$ cycloalkyl, wherein each alkyl or cycloalkyl is unsubstituted or substituted with 1-5 fluorine atoms;

T is —O—, —S—, —N($R^{14}$)—, $CH_2$ or $CF_2$;

$R^{14}$ is hydrogen, $C_1$-$C_3$-alkyl, or $C_3$-$C_5$ cycloalkyl, wherein each alkyl or cycloalkyl is unsubstituted or substituted with 1-5 fluorine atoms;

Y is selected from $Y^1$ to $Y^6$

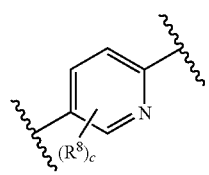
(Y¹)

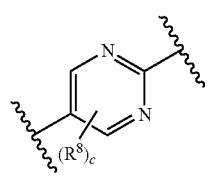
(Y²)

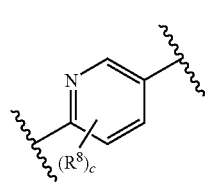
(Y³)

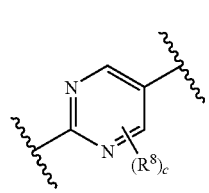
(Y⁴)

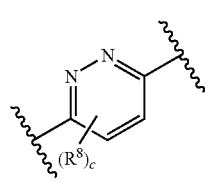
(Y⁵)

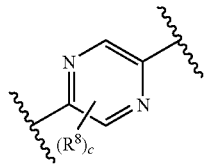
(Y⁶)

$R^8$ is independently selected from hydrogen, halogen, cyano, nitro, azido, $C_1$-$C_6$ alkyl, $C_2$-$C_6$ alkenyl, $C_2$-$C_6$ alkynyl, $C_3$-$C_6$ cycloalkyl, heterocyclyl, aryl, heteroaryl, $NR^{12}R^{13}$, $NR^{12}S(O)_mR^{13}$, $NR^{12}C(O)OR^{13}$, $NR^{12}C(O)R^{13}$, $NR^{12}C(O)NR^{12}R^{13}$, $OR^{12}$, $OC(O)R^{12}$, $S(O)_iR^{12}$, $SO_2NR^{12}C(O)R^{13}$, $S(O)_mNR^{12}R^{13}$, $C(O)R^{12}$, $C(O)OR^{12}$, $C(O)NR^{12}R^{13}$, and $C(NR^{12})NR^{12}R^{13}$, wherein each alkyl, alkenyl, alkynyl, cycloalkyl, heterocyclyl, aryl or heteroaryl is unsubstituted or substituted with one to five substituents $R^{11}$;

Z is phenyl-A-$R^9$, pyridyl-A-$R^9$, pyrimidyl-A-$R^9$ or pyridazyl-A-$R^9$, wherein phenyl, pyridyl, pyrimidyl or pyridazyl is unsubstituted or substituted with one, two or three groups selected from halogen, $C_1$-$C_4$ alkyl, $C_3$-$C_5$ cycloalkyl, $C_2$-$C_4$ alkenyl, $C_2$-$C_4$ alkynyl, cyano, OH, $OCH_3$, $OCH_2F$, $OCHF_2$, $OCF_3$, $SCF_3$, $NH_2$, $NHCH_3$ and $N(CH_3)_2$;

A is a bond, $CH_2$, $CHCH_3$, $C(CH_3)_2$ or $CF_2$;

$R^9$ is hydrogen, $COOR^{17}$, $CONR^{17}R^{18}$, $C(O)NHSO_2R^{17}$, $SO_2NHC(O)R^{17}$, $S(O)_mR^{17}$, $C(NR^{17})NR^{17}R^{18}$, or tetrazole which is connected to A via the C-atom;

$R^{17}$ and $R^{18}$ are independently from each other selected from hydrogen, $C_1$-$C_6$-alkyl, $C_2$-$C_6$-alkenyl, $C_2$-$C_6$ alkynyl, and $C_3$-$C_6$-cycloalkyl; or $R^{17}$ and $R^{18}$ together may form a 3-7-membered heterocyclic or heteroaromatic ring, wherein the alkyl, alkenyl, cycloalkyl, heterocyclyl and heteroaryl groups are unsubstituted or substituted with one to five substituents $R^{11}$;

a is 0 or 1;
b is 1, 2, or 3;
c is 1 or 2;
i is 0, 1, or 2; and
m is 1 or 2.

Preferably, $R^1$ and $R^2$ are independently from each other selected from hydrogen, fluorine, cyano, nitro, azido, $NR^5R^6$, $OR^5$, $SR^5$, $C_1$-$C_6$ alkyl, $C_2$-$C_6$ alkenyl, $C_2$-$C_6$ alkynyl, $C_3$-$C_6$ cycloalkyl; or $R^1$ and $R^2$ are together =S; or $R^1$ and $R^2$ may together form a 3-6-membered carbocyclic or heterocyclic ring which each can be unsaturated or saturated, wherein each alkyl, alkenyl, alkynyl, cycloalkyl group, carbocyclic or heterocyclic ring is unsubstituted or substituted with one to five substituents $R^{11}$;

More preferably, $R^1$ and $R^2$ are independently from each other selected from hydrogen, fluorine and $C_{1-6}$ alkyl wherein the alkyl group is unsubstituted or substituted with one to five substituents $R^{11}$. Most preferred, $R^1$ and $R^2$ are independently from each other selected from hydrogen and methyl.

It is preferred that in each $X^1$, $X^2$ and $X^4R^3$ is hydrogen, $C_1$-$C_6$ alkyl, $NR^{19}R^{20}$ or $C_3$-$C_6$ cycloalkyl, wherein each alkyl or cycloalkyl is unsubstituted or substituted with one to five substituents $R^{11}$, preferably one, two or three substituents $R^{11}$, and that in each $X^3R^3$ is hydrogen, $C_{1-6}$ alkyl or $C_3$-$C_6$ cycloalkyl, wherein each alkyl or cycloalkyl is unsubstituted or substituted with one to five substituents $R^{11}$, preferably one, two or three substituents $R^{11}$.

It is further preferred that $R^{19}$ and $R^{20}$ are independently from each other selected from hydrogen, $C_1$-$C_6$ alkyl and $C_3$-$C_6$ cycloalkyl. In an alternative embodiment, $R^{19}$ and $R^{20}$ preferably form together a 3-7-membered heterocyclic or heteroaromatic ring. The alkyl, cycloalkyl, heterocyclic or heteroaromatic groups are unsubstituted or substituted with one to five substituents $R^{11}$, preferably one, two or three substituents $R^{11}$.

In a preferred embodiment, Q is O or NH.

In each of $X^1$ to $X^4$, $R^4$ is preferably selected from hydrogen, halogen, $C_{1-6}$ alkyl, O—$C_1$-$C_6$ alkyl, and CN, wherein each alkyl group is unsubstituted or substituted by one to five substituents $R^{11}$, preferably one, two or three substituents $R^{11}$. More preferably, $R^4$ is selected from hydrogen, halogen and $C_{1-6}$ alkyl wherein each alkyl group is unsubstituted or substituted by one, two or three substituents $R^{11}$.

The index b preferably is 1 or 2; most preferably b is 2.

The radical $R^4$ may be located on any position of the phenyl ring. Preferably, $R^4$ is located on the 2- and/or 4- and/or 6-position of the phenyl ring. Most preferably, $R^4$ is located on the 2- and 6-position of the phenyl ring.

In a preferred embodiment T is O, $CH_2$ or $NR^{14}$ wherein $R^{14}$ is as defined above.

Y is preferably selected from $Y^1$, $Y^3$ and $Y^5$ wherein $R^8$ and c are defined as above.

Preferably, $R^8$ is independently selected from hydrogen, halogen, $C_1$-$C_6$ alkyl, $OR^{12}$, $NR^{12}R^{13}$, $C(O)R^{12}$ and $C(O)OR^{12}$ wherein each alkyl is unsubstituted or substituted by one to five substituents $R^{11}$, preferably one, two or three substituents $R^{11}$ and wherein $R^{12}$ and $R^{13}$ are defined as above. More preferably, $R^{12}$ and $R^{13}$ are independently selected from hydrogen and $C_1$-$C_6$ alkyl. In a further preferred embodiment $R^8$ is independently selected from hydrogen, halogen, $C_1$-$C_6$-alkyl, or O—$C_1$-$C_3$-alkyl, wherein each alkyl group is unsubstituted or substituted with one to five substituents $R^{11}$, preferably one, two or three substituents $R^{11}$.

It is preferred that Z is phenyl-A-$R^9$, wherein phenyl is unsubstituted or substituted with one to three groups selected from halogen, cyano, $C_{1-4}$ alkyl, OH, $OCH_3$, $OCH_2F$, $OCHF_2$, $OCF_3$, $SCF_3$, $NH_2$, $NHCH_3$ and $N(CH_3)_2$.

In a preferred embodiment, $R^9$ is selected from $COOR^{12}$, $CONH_2$ and $CONR^{17}R^{18}$. Therein, $R^{17}$ is preferably independently selected from the group consisting of $C_{1-6}$ alkyl and $C_{3-6}$ cycloalkyl and $R^{18}$ is preferably selected from the group consisting of hydrogen, $C_{1-6}$ alkyl and $C_{3-6}$ cycloalkyl or $R^{17}$ and $R^{18}$ form together a 5-6 membered heterocyclic ring. Further, it is preferred that the $C_1$-$C_6$ alkyl group in said embodiment is unsubstituted or substituted by one to five substituents $R^{11}$ whereby $R^{11}$ is selected from the group consisting of OH, $NH_2$, $NH(C_1$-$C_6$ alkyl) and $N(C_1$-$C_6$ alkyl)$_2$.

In an alternatively preferred embodiment, $R^9$ is selected from the group consisting of hydrogen, COOH and $C(O)NHSO_2R^{17}$. More preferably, $R^9$ is selected from the group consisting of COOH and $C(O)NHSO_2C_1$-$C_6$ alkyl.

Preferred compounds of formula (I) are those compounds in which one or more of the residues contained therein have the meanings given above. It is understood, that the claimed compounds cover any compound obtained by combining any of the definitions disclosed within this description for the various substituents. With respect to all compounds of formula (I), the present invention also includes all tautomeric and stereoisomeric forms, solvates and mixtures thereof in all ratios, and their pharmaceutically acceptable salts.

In the above and the following, the employed terms have independently the meaning as described below:

Aryl is an aromatic mono- or polycyclic moiety with preferably 6 to 20 carbon atoms which is preferably selected from phenyl, biphenyl, naphthyl, tetrahydronaphthyl, fluorenyl, indenyl and phenanthrenyl, more preferably phenyl and naphthyl.

Heteroaryl is a monocyclic or polycyclic aromatic moiety having 5 to 20 carbon atoms with at least one ring containing a heteroatom selected from O, N and/or S, or heteroaryl is an aromatic ring containing at least one heteroatom selected from O, N and/or S and 1 to 6 carbon atoms. Preferably, heteroaryl contains 1 to 4, more preferably 1, 2 or 3 heteroatoms selected from O and/or N and is preferably selected from pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl and furopyridinyl. Spiro moieties are also included within the scope of this definition. Preferred heteroaryl includes pyridinyl, imidazolyl, pyrimidinyl, pyrazolyl, triazolyl, pyrazinyl, tetrazolyl, isoxazolyl, oxazolyl, isothiazolyl, oxadiazolyl and triazolyl.

Heterocycyl is a 3 to 10-membered saturated or unsaturated ring containing at least one heteroatom selected from O, N and/or S and 1 to 6 carbon atoms. Preferably, heterocyclyl contains 1 to 4, more preferably 1, 2 or 3 heteroatoms selected from O and/or N. Heterocyclyl includes mono- and bicyclic ringsystems and is preferably selected from pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, azetidin-2-one-1-yl, pyrrolidin-2-one-1-yl, piperid-2-one-1-yl, azepan-2-one-1-yl, 3-azabicyco[3.1.0]hexanyl, 3-azabicyclo[4.1.0]heptanyl, azabicyclo[2.2.2]hexanyl, 3H-indolyl and quinolizinyl. Spiromoieties are also included within the scope of this definition.

$C_1$-$C_6$ Alkyl is a saturated hydrocarbon moiety, namely straight chain or branched alkyl having 1 to 6 carbon atoms, preferably 1 to 4 carbon atoms, such as methyl, ethyl, n-propyl, isopropyl, n-butyl, isobutyl, tert-butyl, n-pentyl, isopentyl, neopentyl or hexyl.

$C_3$-$C_5$ Cycloalkyl is an alkyl ring having 3 to 6 carbon atoms, such as cydopropyl, cyclobutyl, cyclopentyl or cyclohexyl.

Carbocyclyl is a monocyclic or polycyclic ring system of 3 to 20 carbon atoms which may be saturated or unsaturated. Thus, the term "carbocyclyl" includes cycloalkyls as defined above as well as partially unsaturated carbocyclic groups such as cyclopentene, cyclopentadiene or cyclohexene.

$C_2$-$C_6$ Alkenyl is an unsaturated hydrocarbon moiety with one or more double bonds, preferably one double bond, namely straight chain or branched alkenyl having 2 to 6 carbon atoms, preferably 2 to 4 atoms, such as vinyl, allyl, methallyl, buten-2-yl, buten-3-yl, penten-2-yl, penten-3-yl, penten-4-yl, 3-methyl-but-3-enyl, 2-methyl-but-3-enyl, 1-methyl-but-3-enyl or hexenyl.

$C_2$-$C_6$ Alkynyl is an unsaturated hydrocarbon moiety with one or more triple bonds, preferably one triple bond, namely straight chain or branched alkynyl having 2 to 6 carbon atoms, more preferably 2 to 4 atoms, such as ethynyl, propynyl, butyn-2-yl, butyn-3-yl, pentyn-2-yl, pentyn-3-yl, pentyn-4-yl, 2-methyl-but-3-ynyl, 1-methyl-but-3-ynyl or hexynyl.

Halo or halogen is a halogen atom selected from F, Cl, Br and I, preferably F, Cl and Br. Preferred embodiments of the compounds according to the present invention are shown below.

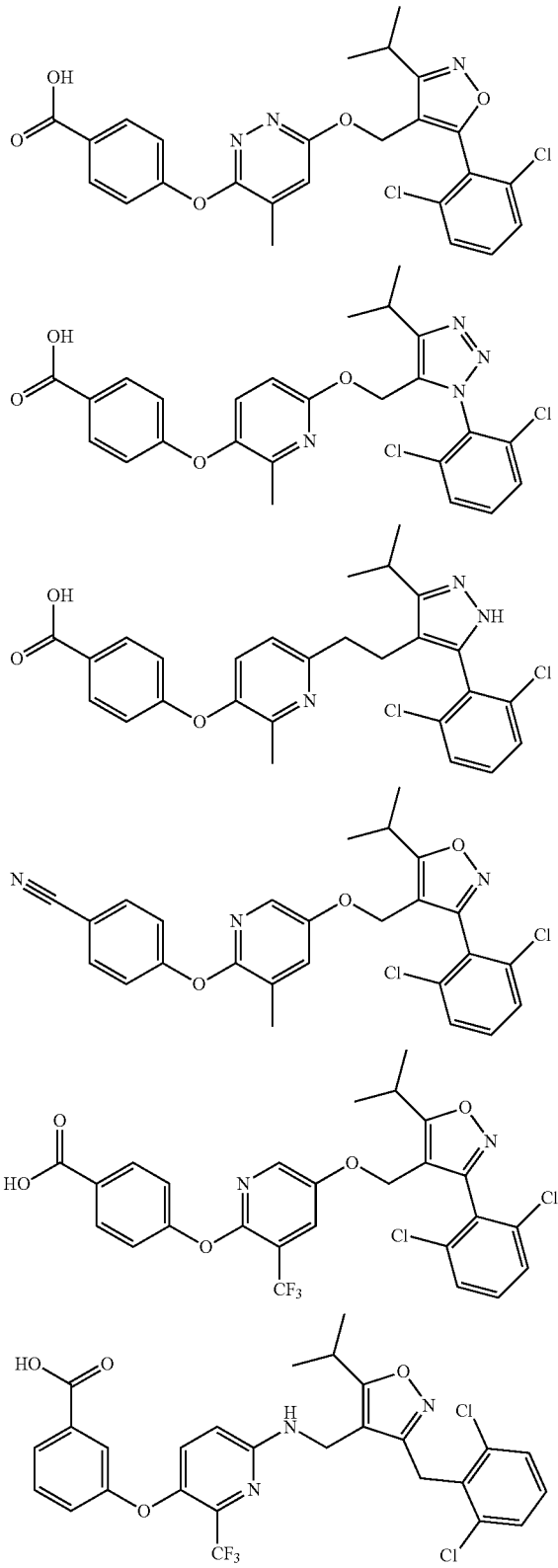

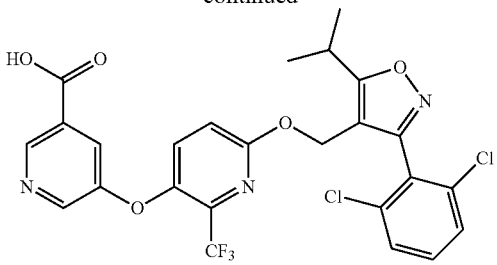

The compounds of the present invention can be in the form of a prodrug compound. "Prodrug compound" means a derivative that is converted into a compound according to the present invention by a reaction with an enzyme, gastric acid or the like under a physiological condition in the living body, e.g. by oxidation, reduction, hydrolysis or the like, each of which is carried out enzymatically. Examples of the prodrug are compounds, wherein the amino group in a compound of the present invention is acylated, alkylated or phosphorylated to form, e.g., eicosanoylamino, alanylamino, pivaloyloxymethylamino or wherein the hydroxyl group is acylated, alkylated, phosphorylated or converted into the borate, e.g. acetyloxy, palmitoyloxy, pivaloyloxy, succinyloxy, fumaryloxy, alanyloxy or wherein the carboxyl group is esterified or amidated. These compounds can be produced from compounds of the present invention according to well-known methods. Other examples of the prodrug are compounds, wherein the carboxylate in a compound of the present invention is, for example, converted into an alkyl-, aryl-, choline-, amino, acyloxymethylester, linolenoyl-ester.

Metabolites of compounds of the present invention are also within the scope of the present invention.

Where tautomerism, like e.g. keto-enol tautomerism, of compounds of the present invention or their prodrugs may occur, the individual forms, like e.g. the keto and enol form, are each within the scope of the invention as well as their mixtures in any ratio. Same applies for stereoisomers, like e.g. enantiomers, cis/trans isomers, conformers and the like.

If desired, isomers can be separated by methods well known in the art, e.g. by liquid chromatography. Same applies for enantiomers by using e.g. chiral stationary phases. Additionally, enantiomers may be isolated by converting them into diastereomers, i.e. coupling with an enantiomerically pure auxiliary compound, subsequent separation of the resulting diastereomers and cleavage of the auxiliary residue. Alternatively, any enantiomer of a compound of the present invention may be obtained from stereoselective synthesis using optically pure starting materials.

The compounds of the present invention can be in the form of a pharmaceutically acceptable salt or a solvate. The term "pharmaceutically acceptable salts" refers to salts prepared from pharmaceutically acceptable non-toxic bases or acids, including inorganic bases or acids and organic bases or acids. In case the compounds of the present invention contain one or more acidic or basic groups, the invention also comprises their corresponding pharmaceutically or toxicologically acceptable salts, in particular their pharmaceutically utilizable salts. Thus, the compounds of the present invention which contain acidic groups can be present on these groups and can be used according to the invention, for example, as alkali metal salts, alkaline earth metal salts or ammonium salts. More precise examples of such salts include sodium salts, potassium salts, calcium salts, magnesium salts or salts with ammonia or organic amines such as, for example, ethylamine, ethanolamine, triethanolamine or amino acids. The compounds of the present invention which contain one or more basic groups, i.e. groups which can be protonated, can be present and can be used according to the invention in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the present invention simultaneously contain acidic and basic groups in the molecule, the invention also includes, in addition to the salt forms mentioned, inner salts or betaines (zwitterions). The respective salts can be obtained by customary methods which are known to the person skilled in the art like, for example, by contacting these with an organic or inorganic acid or base in a solvent or dispersant, or by anion exchange or cation exchange with other salts. The present invention also includes all salts of the compounds of the present invention which, owing to low physiological compatibility, are not directly suitable for use in pharmaceuticals but which can be used, for example, as intermediates for chemical reactions or for the preparation of pharmaceutically acceptable salts.

Furthermore, the present invention provides pharmaceutical compositions comprising at least one compound of the present invention, or a prodrug compound thereof, or a pharmaceutically acceptable salt or solvate thereof as active ingredient together with a pharmaceutically acceptable carrier.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing at least one compound of the present invention and a pharmaceutically acceptable carrier.

The pharmaceutical composition of the present invention may additionally comprise one or more other compounds as active ingredients like a prodrug compound or other nuclear receptor modulators.

The compositions are suitable for oral, rectal, topical, parenteral (including subcutaneous, intramuscular, and intravenous), ocular (ophthalmic), pulmonary (nasal or buccal inhalation) or nasal administration, although the most suitable route in any given case will depend on the nature and severity of the conditions being treated and on the nature of the active ingredient. They may be conveniently presented in unit dosage form and prepared by any of the methods well-known in the art of pharmacy.

The compounds of the present invention bind to the NR1H4 receptor (FXR) and act as agonists or partial agonists of the NR1H4 receptor (FXR).

FXR is proposed to be a nuclear bile acid sensor. As a result, it modulates both, the synthetic output of bile acids in the liver and their recycling in the intestine (by regulating bile acid binding proteins). But beyond bile acid physiology, FXR seems to be involved in the regulation of many diverse physiological processes which are relevant in the etiology and for the treatment of diseases as diverse as cholesterol gallstones, metabolic disorders such as Type II Diabetes, dyslipidemias or obesity, chronic inflammatory diseases such as Inflammatory Bowel Diseases or chronic intrahepatic forms of cholestasis and many others diseases (T. Claudel) et al. "The Farnesoid X receptor a molecular link between bile acid and lipid and glucose metabolism" Arterioscler. Thromb. Vasc. Biol. 2005, 25(10), 2020-2030; S. Westin et al. "FXR, a therapeutic target for bile acid and lipid disorders" Mini Rev. Med. Chem. 2005, 5(8), 719-727).

FXR regulates a complex pattern of response genes in the liver. The gene products have impact on diverse physiological processes. In the course of functional analysis of FXR, the first regulatory network that was analyzed was the regulation of bile acid synthesis. While the LXRs induce the key enzyme of the conversion of cholesterol into bile acids, Cyp7A1, via the induction of the regulatory nuclear receptor LRH-1, FXR represses the induction of Cyp7A1 via the upregulation of mRNA encoding SHP, a further nuclear receptor that is dominant repressive over LRH-1. Since FXR binds the end products of this pathway, primary bile acids such as cholic acid (CA) or chenodeoxycholic acid (CDCA), this can be regarded as an example of feedback inhibition on the gene expression level (B. Goodwin et al. "A regulatory cascade of the nuclear receptors FXR, SHP-1, and LRH-1 represses bile acid biosynthesis" Mol. Cell. 2000, 6(3), 517-526; T. Lu et al. "Molecular basis for feedback regulation of bile acid synthesis by nuclear receptors" Mol. Cell. 2000, 6(3), 507-515). Parallel to the repression of bile acid synthesis via SHP, FXR induces a range of so-called ABC (for ATP-binding cassette) transporters that are responsible for the export of toxic bile acids from the hepatocyte cytosol into the canaliculi, the small bile duct ramifications where the bile originates. This hepatoprotective function of FXR became first apparent with the analysis of FXR knockout mice (C. Sinai et al. "Targeted disruption of the nuclear receptor FXR/BAR impairs bile acid and lipid homeostasis" Cell 2000, 102(6), 731-744) where under- or overexpression of several ABC-transporters in the liver was shown. Further detailed analysis revealed that the major bile salt excretory pump BSEP or ABCB11 (M. Ananthanarayanan et al. "Human bile salt export pump promoter is transactivated by the farnesoid X receptor/bile acid receptor" J. Biol. Chem. 2001, 276(31), 28857-28865; J. Plass et al. "Farnesoid X receptor and bile salts are involved in transcriptional regulation of the gene encoding the human bile salt export pump" Hepatology 2002, 35(3), 589-96) as well as the key enzyme which mediates lipid transfer from lipoproteins to phospholipids, PLTP (N. Urizar et al. "The farnesoid X-activated receptor mediates bile acid activation of phospholipid transfer protein gene expression" J. Biol. Chem. 2000, 275 (50), 39313-39317), and the two key canalicular membrane transporters for phospholipids, MRP-2 (ABCC4) (H. Kast et al. "Regulation of multidrug resistance-associated protein 2 (ABCC2) by the nuclear receptors pregnane X receptor, farnesoid X-activated receptor, and constitutive androstane receptor" J. Biol. Chem. 2002, 277(4), 2908-2915) and MDR-3 (ABCB4); L. Huang et al. "Farnesoid X receptor activates transcription of the phospholipid pump MDR3" J. Biol. Chem. 2003, 278(51), 51085-51090) are direct targets for ligand-directed transcriptional activation by FXR (summarized in: M. Miyata "Role of farnesoid X receptor in the enhancement of canalicular bile acid output and excretion of unconjugated bile acids: a mechanism for protection against cholic acid-induced liver toxicity", J. Pharmacol. Exp. Ther. 2005, 312(2), 759-766; G. Rizzo et al. "Role of FXR in regulating bile acid homeostasis and relevance for human diseases" Curr. Drug Targets Immune Endocr. Metabol. Disord. 2005, 5(3), 289-303.)

The fact that FXR seems to be the major metabolite sensor and regulator for the synthesis, export and re-circulation of bile acids suggested the use of FXR ligands to induce bile flow and change bile acid composition towards more hydrophilic composition. With the development of the first synthetic FXR ligand GW4064 (P. Maloney et al. "Identification of a chemical tool for the orphan nuclear receptor FXR" J. Med. Chem. 2000, 43(16), 2971-2974; T. Willson et al. "Chemical genomics: functional analysis of orphan nuclear receptors in the regulation of bile acid metabolism" Med. Res. Rev. 2001, 21(6) 513-22) as a tool compound and of the semi-synthetic artificial bile acid ligand 6-alpha-ethyl-CDCA, the effects of superstimulation of FXR by potent agonists could be analyzed. It was shown that both ligands induce bile flow in bile duct ligated animals. Moreover, in addition to choleretic effects, also hepatoprotective effects could be demonstrated (R. Pellicciari et al. "6alpha-ethyl-chenodeoxycholic acid (6-ECDCA), a potent and selective FXR agonist endowed with anticholestatic activity" J. Med. Chem. 2002, 45(17), 3569-3572; Y. Liu et al. "Hepatoprotection by the farnesoid X receptor agonist GW4064 in rat models of intra- and extrahepatic cholestasis" J. Clin. Invest. 2003, 112(11), 1678-1687). This hepatoprotective effect was further narrowed down to an anti-fibrotic effect that results from the repression of Tissue Inhibitors of Matrix-Metalloproteinases, TIMP-1 and 2, the induction of collagen-deposit resolving Matrix-Metalloproteinase 2 (MMP-2) in hepatic stellate cells and the subsequent reduction of alpha-collagen mRNA and Transforming growth factor beta (TGF-beta) mRNA which are both pro-fibrotic factors by FXR agonists (S. Fiorucci et al. "The nuclear receptor SHP mediates inhibition of hepatic stellate cells by FXR and protects against liver fibrosis", Gastroenterology 2004, 127(5), 1497-1512; S. Fiorucci et al. "A farnesoid x receptor-small heterodimer partner regulatory cascade modulates tissue metalloproteinase inhibitor-1 and matrix metalloprotease expression in hepatic stellate cells and promotes resolution of liver fibrosis" J. Pharmacol. Exp. Ther. 2005, 314(2), 584-595). The antifibrotic activity of FXR is at least partially mediated by the induction of PPARgamma, a further nuclear receptor, with which anti-fibrotic activity is associated (S. Fiorucci et al. "Cross-talk between farnesoid-X-receptor (FXR) and peroxisome proliferator-activated receptor gamma contributes to the antifibrotic activity of FXR ligands in rodent models of liver cirrhosis" J. Pharmacol. Exp. Ther. 2005, 315(1), 58-68; A. Galli et al. "Antidiabetic thiazolidinediones inhibit collagen synthesis and hepatic stellate cell activation in vivo and in vitro" Gastroenterology 2002, 122(7), 1924-1940; I. Pineda Torra et al., "Bile acids induce the expression of the human peroxisome proliferator-activated receptor alpha gene via activation of the farnesoid X receptor" Mol. Endocrinol. 2003, 17(2), 259-272). Furthermore, anti-cholestatic activity was demonstrated in bile-duct ligated animal models as well as in animal models of estrogen-induced cholestasis (S. Fiorucci et al. "Protective effects of 6-ethyl chenodeoxycholic acid, a farnesoid X receptor ligand, in estrogen-induced cholestasis" J. Pharmacol. Exp. Ther. 2005, 313(2), 604-612).

Genetic studies demonstrate that in hereditary forms of cholestasis (Progressive Familiar Intrahepatic Cholestasis=PFIC, Type I-IV) either nuclear localization of FXR itself is reduced as a consequence of a mutation in the FIC1 gene (in PFIC Type I, also called Byler's Disease) (F. Chen et al. "Progressive familial intrahepatic cholestasis, type 1, is associated with decreased farnesoid X receptor activity" Gastroenterology. 2004, 126(3), 756-64; L. Alvarez et al. "Reduced hepatic expression of farnesoid X receptor in hereditary cholestasis associated to mutation in ATP8B1" Hum. Mol. Genet. 2004; 13(20), 2451-60) or levels of the FXR target gene encoding MDR-3 phospholipid export pump are reduced (in PFIC Type III). Taken together there is a growing body of evidence that FXR binding compounds will demonstrate substantial clinical utility in the therapeutic regimen of chronic cholestatic conditions such as Primary Biliary Cirrhosis (PBC) or Primary Sclerosing Cholangitis (PSC) (reviewed in: G. Rizzo et al. Curr. Drug Targets Immune Endocr. Metabol. Disord. 2005, 5(3), 289-303; G. Zollner "Role of nuclear receptors in the adaptive response to bile acids and cholestasis: pathogenetic and therapeutic considerations" Mol. Pharm. 2006, 3(3), 231-51, S. Cai et al. "FXR: a target for cholestatic syndromes?" Expert Opin. Ther. Targets 2006, 10(3), 409-421).

The deep impact that FXR activation has on bile acid metabolism and excretion is not only relevant for cholestatic syndromes but even more directly for a therapy against gallstone formation. Cholesterol gallstones form due to low solubility of cholesterol that is actively pumped out of the liver cell into the lumen of the canaliculi. It is the relative percentage of content of the three major components, bile acids, phospholipids and free cholesterol that determines the formation of mixed micelles and hence apparent solubility of free cholesterol in the bile. FXR polymorphisms map as quantitative trait loci as one factor contributing to gallstone disease (H. Wittenburg "FXR and ABCG5/ABCG8 as determinants of cholesterol gallstone formation from quantitative trait locus mapping in mice", Gastroenterology 2003, 125(3), 868-881). Using the synthetic FXR tool compound GW4064 it could be demonstrated that activation of FXR leads to an improvement of the Cholesterol Saturation Index (=CSI) and directly to an abolishment of gallstone formation in C57L gallstone susceptible mice whereas drug treatment in FXR knockout mice shows no effect on gallstone formation (A. Moschetta et al. "Prevention of cholesterol gallstone disease by FXR agonists in a mouse model" Nature Medicine 2004, 10(12), 1352-1358).

These results qualify FXR as a good target for the development of small molecule agonists that can be used to prevent cholesterol gallstone formation or to prevent re-formation of gallstones after surgical removal or shockwave lithotripsy (discussed in: S. Doggrell "New targets in and potential treatments for cholesterol gallstone disease" Curr. Opin. Investig. Drugs 2006, 7(4), 344-348).

Since the discovery of the first synthetic FXR agonist and its administration to rodents it became evident that FXR is a key regulator of serum triglycerides (P. Maloney et al. J. Med. Chem. 2000, 43(16), 2971-2974; T. Willson et al. Med. Res. Rev. 2001, 21(6), 513-22). Over the past six years accumulating evidence has been published that activation of FXR by synthetic agonists leads to significant reduction of serum triglycerides, mainly in the form of reduced VLDL, but also to reduced total serum cholesterol (H. Kast et al. "Farnesoid X-activated receptor induces apolipoprotein C-II transcription: a molecular mechanism linking plasma triglyceride levels to bile acids" Mol. Endocrinol. 2001, 15(10), 1720-1728; N. Urizar et al. "A natural product that lowers cholesterol as an antagonist ligand for FXR" Science 2002, 296(5573), 1703-1706; G. Lambert et al. "The farnesoid X-receptor is an essential regulator of cholesterol homeostasis" J. Biol. Chem. 2003, 278, 2563-2570; M. Watanabe et al. "Bile acids lower triglyceride levels via a pathway involving FXR, SHP, and SREBP-1c" J. Clin. Invest. 2004, 113(10), 1408-1418; A. Figge et al. "Hepatic overexpression of murine Abcb11 increases hepatobiliary lipid secretion and reduces hepatic steatosis" J. Biol. Chem. 2004, 279(4), 2790-2799; S. Bilz et al. "Activation of the farnesoid X receptor improves lipid metabolism in combined hyperlipidemic hamsters" Am. J. Physiol. Endocrinol. Metab. 2006, 290(4), E716-22).

But the lowering of serum triglycerides is not a stand alone effect. Treatment of db/db or ob/ob mice with synthetic FXR agonist GW4064 resulted in marked and combined reduction of serum triglycerides, total cholesterol, free fatty acids, ketone bodies such as 3-OH Butyrate. Moreover, FXR activation engages with the intracellular insulin signaling pathway in hepatocytes, resulting in reduced output of glucose from liver gluconeogenesis but concomitant increase in liver glycogen. Insulin sensitivity as well as glucose tolerance were positively impacted by FXR treatment (K. Stayrook et al. "Regulation of carbohydrate metabolism by the farnesoid X receptor" Endocrinology 2005, 146(3), 984-91; Y. Zhang et al. "Activation of the nuclear receptor FXR improves hyperglycemia and hyperlipidemia in diabetic mice" Proc. Natl. Acad. Sci. USA 2006, 103(4), 1006-1011; B. Cariou et al. "The farnesoid X receptor modulates adiposity and peripheral insulin sensitivity in mice" J. Biol. Chem. 2006, 281, 11039-11049; K. Ma et al. "Farnesoid X receptor is essential for normal glucose homeostasis" J. Clin. Invest. 2006, 116(4), 1102-1109; D. Duran-Sandoval et al. "Potential regulatory role of the farnesoid X receptor in the metabolic syndrome" Biochimie 2005, 87(1), 93-98). An effect on reduction of body weight was also recently observed in mice overfed with a high lipid diet (C. Lihong et al. "FXR Agonist, GW4064, Reverses Metabolic Defects in High-Fat Diet Fed Mice" American Diabetes Association (ADA) 66th annual scientific sessions, June 2006, Abstract Number 856-P). This weight loss effect might results from FXR's induction of FGF-19, a fibroblast growth factor that is known to lead to weight loss and athletic phenotype (J. Holt et al. Genes Dev. 2003, 17(13), 1581-1591; E. Tomlinson et al. "Transgenic mice expressing human fibroblast growth factor-19 display increased metabolic rate and decreased adiposity" Endocrinology 2002, 143 (5), 1741-1747). In recent patent applications, the effect of FXR agonist on reduction of body weight was demonstrated (Stoffel W. et al. "Methods for inhibiting Adipogenesis and for treating Type 2 Diabetes" International Patent Application WO 2004/087076; S. Jones et al "Methods of using FXR Agonists" International Patent Application WO 2003/080803).

Taken together, these pharmacological effects of FXR agonists can be exploited in different therapeutic ways: FXR binding compounds are thought to be good candidates for the treatment of Type II Diabetes because of their insulin sensitization, glycogenogenic, and lipid lowering effects.

In one embodiment, the compounds according to the invention and pharmaceutical compositions comprising said compounds are used in the treatment of Type II Diabetes which can be overcome by FXR-mediated upregulation of systemic insulin sensitivity and intracellular insulin signalling in liver, increased peripheral glucose uptake and metabolisation, increased glycogen storage in liver, decreased output of glucose into serum from liver-borne gluconeogenesis.

In a further embodiment, said compounds and pharmaceutical compositions are used for the preparation of a medicament for the treatment of chronic intrahepatic and some forms of extrahepatic cholestatic conditions, such as primary biliary cirrhosis (PBC), primary sclerosing cholangitis (PSC), progressive familiar cholestasis (PFIC), alcohol-induced cirrhosis and associated cholestasis, or liver fibrosis resulting from chronic cholestatic conditions or acute intraheptic cholestatic conditions such as estrogen or drug induced cholestasis.

The invention also relates to a compound of formula (I) or to a pharmaceutical composition comprising said compound for the treatment of gastrointestinal conditions with a reduced uptake of dietary fat and fat-soluble dietary vitamins which can be overcome by increased intestinal levels of bile acids and phospholipids.

In a further embodiment, said compound or pharmaceutical composition is used for treating a disease selected from the group consisting of lipid and lipoprotein disorders such as hypercholesterolemia, hypertriglyceridemia, and atherosclerosis as a clinically manifest condition which can be ameliorated by FXR's beneficial effect on raising HDL cholesterol, lowering serum triglycerides, increasing conversion of liver cholesterol into bile acids and increased clearance and metabolic conversion of VLDL and other lipoproteins in the liver.

In one further embodiment, said compound and pharmaceutical composition are used for the preparation of a medicament where the combined lipid lowering, anti-cholestatic and anti-fibrotic effects of FXR-targeted medicaments can be exploited for the treatment of liver steatosis and associated syndromes such as non-alcoholic steatohepatitis ("NASH"), or for the treatment of cholestatic and fibrotic effects that are associated with alcohol-induced cirrhosis, or with viral-borne forms of hepatitis.

In conjunction with the hypolipidemic effects it was also shown that loss of functional FXR leads to increased atherosclerosis in ApoE knockout mice (E. Hanniman et al. "Loss of functional farnesoid X receptor increases atherosclerotic lesions in apolipoprotein E-deficient mice" J. Lipid Res. 2005, 46(12), 2595-2604). Therefore, FXR agonists might have clinical utility as anti-atherosclerotic and cardioprotective drugs. The downregulation of Endothelin-1 in Vascular Smooth Muscle Cells might also contribute to such beneficial therapeutic effects (F. He et al. "Downregulation of endothelin-1 by farnesoid X receptor in vascular endothelial cells" Circ. Res. 2006, 98(2), 192-9).

The invention also relates to a compound according to formula (I) or a pharmaceutical composition comprising said compound for preventive and posttraumatic treatment of cardiovascular disorders such as acute myocardial infarction, acute stroke, or thrombosis which occur as an endpoint of chronic obstructive atherosclerosis.

In a few selected publications the effects of FXR and FXR agonists on proliferation of cancer and non-malignant cells and apoptosis have been assessed. From these preliminary results it seems as if FXR agonists might also influence apoptosis in cancer cell lines (E. Niesor et al. "The nuclear receptors FXR and LXRalpha: potential targets for the development of drugs affecting lipid metabolism and neoplastic diseases" Curr. Pharm. Des. 2001, 7(4), 231-59) and in Vascular Smooth Muscle Cells (VSMCs) (D. Bishop-Bailey et al. "Expression and activation of the farnesoid X receptor in the vasculature" Proc. Natl. Acad. Sci. USA. 2004, 101(10), 3668-3673). Furthermore, FXR seems to be expressed in metastasizing breast cancer cells and in colon cancer (J. Silva "Lipids isolated from bone induce the migration of human breast cancer cells" J. Lipid Res. 2006, 47(4), 724-733; G. De Gottardi et al. "The bile acid nuclear receptor FXR and the bile acid binding protein IBABP are differently expressed in colon cancer" Dig. Dis. Sci. 2004, 49(6), 982-989). Other publications that focus primarily on FXR's effect on metabolism draw a line to intracellular signaling from FXR via the Forkhead/Wingless (FOXO) family of transcriptional modulators to the Phosphatidylinositol-trisphosphat ($PI_3$)-Kinase/Akt signal transduction pathway (D. Duran-Sandoval et al. J. Biol. Chem. 2005, 280(33), 29971-29979; Y. Zhang et al. Proc. Natl. Acad. Sci. USA. 2006, 103(4), 1006-1011) that is similarly employed by insulin intracellular signaling as well as neoplastically transformed cells.

This would allow to regard FXR also as a potential target for the treatment of proliferative diseases, especially metastasizing cancer forms that overexpress FXR or those where the FOXO/PI$_3$-Kinase/Akt Pathway is responsible for driving proliferation.

Therefore, the compounds according to formula (I) or pharmaceutical composition comprising said compounds are suitable for treating Non-malignant hyperproliferative disorders such as increased neointima formation after balloon vessel dilatation and stent application due to increased proliferation of vascular smooth muscle cells (VSMCs) or Bening Prostate Hyperplasia (BPH), a pre-neoplastic form of hyperproliferation, other forms of scar tissue formation and fibrotisation which can be overcome by e.g. FXR-mediated intervention into the PI-3Kinase/AKT/mTOR intracellular signalling pathway, reduction in Matrix-Metalloproteinase activity and alpha-Collagen deposition.

In a further embodiment, said compounds and pharmaceutical compositions are used for the treatment of malignant hyperproliferative disorders such as all forms of cancer (e.g. certain forms of breast or prostate cancer) where interference with PI-3-Kinase/AKT/mTOR signalling and/or induction of p27$^{kip}$ and/or induction of apoptosis will have a beneficial impact.

Finally, FXR seems also to be involved in the control of antibacterial defense in the intestine (T. Inagaki et al. "Regulation of antibacterial defense in the small intestine by the nuclear bile acid receptor" Proc. Natl. Acad. Sci. USA. 2006, 103(10), 3920-3905) although an exact mechanism is not provided. From these published data, however, one can conclude that treatment with FXR agonists might have a beneficial impact in the therapy of Inflammatory Bowel Disorders (IBD), in particular those forms where the upper (ileal) part of the intestine is affected (e.g. ileal Crohn's disease) because this seems to be the site of action of FXR's control on bacterial growth. In IBD the desensitization of the adaptive immune response is somehow impaired in the intestinal immune system. Bacterial overgrowth might then be the causative trigger towards establishment of a chronic inflammatory response. Hence, dampening of bacterial growth by FXR-borne mechanisms might be a key mechanism to prevent acute inflammatory episodes.

Thus, the invention also relates to a compound according to formula (I) or a pharmaceutical composition comprising said compound for treating a disease related to Inflammatory Bowel Diseases such as Crohn's disease or Colitis ulcerosa. FXR-mediated restoration of intestinal barrier function and reduction in non-commensal bacterial load is believed to be helpful in reducing the exposure of bacterial antigens to the intestinal immune system and can therefore reduce inflammatory responses.

The invention further relates to a compound or pharmaceutical composition for the treatment of obesity and associated disorders such as metabolic syndrome (combined conditions of dyslipidemias, diabetes and abnormally high body-mass index) which can be overcome by FXR-mediated lowering of serum triglycerides, blood glucose and increased insulin sensitivity and FXR-mediated weight loss.

In one embodiment, said compound or pharmaceutical composition is for treating persistent infections by intracellular bacteria or parasitic protozoae such as *Mycobacterium* spec. (Treatment of Tuberculosis or Lepra), *Listeria monocytogenes* (Treatment of Listeriosis), *Leishmania* spec. (Leishmaniosis), *Trypanosoma* spec. (Chagas Disease; Trypanosomiasis; Sleeping Sickness).

In a further embodiment, the compounds or pharmaceutical composition of the present invention are useful in the preparation of a medicament for treating clinical complications of Type I and Type II Diabetes. Examples of such complications include Diabetic Nephropathy, Diabetic Retinopathy, Diabetic Neuropathies, Peripheral Arterial Occlusive Disease (PAOD). Other clinical complications of Diabetes are also encompassed by the present invention.

Furthermore, conditions and diseases which result from chronic fatty and fibrotic degeneration of organs due to enforced lipid and specifically triglyceride accumulation and subsequent activation of profibrotic pathways may also be treated by applying the compounds or pharmaceutical composition of the present invention. Such conditions and diseases encompass Non-Alcoholic Steatohepatitis (NASH) and chronic cholestatic conditions in the liver, Glomerulosclerosis and Diabetic Nephropathy in the kidney, Macula Degeneration and Diabetic Retinopathy in the eye and Neurodegenerative diseases such as Alzheimer's Disease in the brain or Diabetic Neuropathies in the peripheral nervous system.

In practical use, the compounds of the present invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

The compounds of the present invention may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

The effective dosage of active ingredient employed may vary depending on the particular compound employed, the mode of administration, the condition being treated and the severity of the condition being treated. Such dosage may be ascertained readily by a person skilled in the art.

When treating or preventing FXR mediated conditions for which compounds of the present invention are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligram to about 50 milligrams. In the case of a 70 kg adult human, the total daily dose will generally be from about 7 milligrams to about 350 milligrams. This dosage regimen may be adjusted to provide the optimal therapeutic response.

Some abbreviations that appear in this application are as follows.

Abbreviations

| Abbreviation | Designation |
| --- | --- |
| d | Doublet |
| DMF, DMFA | N,N-Dimethyl formamide |
| LC | Liquid Chromatography |
| m | Multiplett |
| MS | Mass Spectrometry |
| NMR | Nuclear Magnetic Resonance |
| q | Quartett |
| rt | Retention Time |
| s | Singlett |
| t | Triplett |
| THF | Tetrahydrofurane |
| TLC | Thin Layer Chromatography |

The compounds of the present invention can be prepared according to the procedures of the following Schemes and Examples, using appropriate materials and are further exemplified by the following specific examples. Moreover, by utilizing the procedures described herein, in conjunction with ordinary skills in the art, additional compounds of the present invention claimed herein can be readily prepared. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds. The instant compounds are generally isolated in the form of their pharmaceutically acceptable salts, such as those described above.

The amine-free bases corresponding to the isolated salts can be generated by neutralization with a suitable base, such as aqueous sodium hydrogen carbonate, sodium carbonate, sodium hydroxide and potassium hydroxide, and extraction of the liberated amine-free base into an organic solvent, followed by evaporation. The amine-free base, isolated in this manner, can be further converted into another pharmaceutically acceptable salt by dissolution in an organic solvent, followed by addition of the appropriate acid and subsequent evaporation, precipitation or crystallization. The amine-free base, isolated in this manner, can be further converted into another pharmaceutically acceptable salt by dissolution in an organic solvent, followed by addition of the appropriate acid and subsequent evaporation, precipitation or crystallization. The carboxylic free acids corresponding to the isolated salts can be generated by neutralization with a suitable acid, such as aqueous hydrochloric acid, sodium hydrogen sulfate, sodium dihydrogen phosphate, and extraction of the liberated carboxylic-free acid into an organic solvent, followed by evaporation. The carboxylic acid, isolated in this manner, can be further converted into another pharmaceutically acceptable salt by dissolution in an organic solvent, followed by addition of the appropriate base and subsequent evaporation, precipitation or crystallization.

An illustration of the preparation of compounds of the present invention is shown below. Unless otherwise indicated in the schemes, the variables have the same meaning as described above. The examples presented below are intended to illustrate particular embodiments of the invention. Suitable starting materials, building blocks and reagents employed in the synthesis as described below are commercially available from Sigma-Aldrich Chemie GmbH, Munich, Germany, from Acros Organics, Belgium or from Fisher Scientific GmbH, 58239 Schwerte, Germany, for example, or can be routinely prepared by procedures described in the literature, for example in "March's Advanced Organic Chemistry: Reactions, Mechanisms, and Structure", 5th Edition; John Wiley & Sons or Theophil Eicher, Siegfried Hauptmann "The Chemistry of Heterocycles; Structures, Reactions, Synthesis and Application", $2^{nd}$ edition, Wiley-VCH 2003; Fieser et al. "Fiesers' Reagents for organic Synthesis" Jonh Wiley & Sons 2000.

In formulas of general synthesis schemes depicted below
$E_L$ is halogen, OH, OC(O)alkyl, OC(O)aryl, O-aryl, O-pentafluorophenyl, O-sulfonylalkyl, O-sulfonylaryl, O-succinylimido, O-benzotriazolyl, nitro, azido, S-alkyl, $SO_2$alkyl, $SO_2$aryl, SC(O)alkyl, SC(O)aryl or cyano;

$E_N$-H is a group acting as a nucleophile; such as OH, SH, $NH_2$, $N(R^{14})H$, NH(CO)O-alkyl, NH(CO)O-aryl, $NH(SO)_2$aryl, $NH(SO)_2$alkyl, $CH_3$ or $CF_2H$;

E is $E_L$, $E_N$-H or —H;

$L_A$ is halogen, OH, B(OMe)$_2$, B(OH)$_2$, BF$_3^-$ or 4,4,5,5-tetramethyl-1,3,2-dioxaborolan-2-yl;

$L_B$ is halogen, OH, B(OMe)$_2$, B(OH)$_2$, BF$_3^-$ or 4,4,5,5-tetramethyl-1,3,2-dioxaborolan-2-yl;

R$^{14}$ is as defined in the claims.

In preferred embodiments of the synthesis method $E_L$ is halogen, OH, OSO$_2$alkyl or OSO$_2$aryl;

$E_N$-H is OH, SH, NH$_2$, or CH$_3$;

$L_A$ is halogen or OH

Subsequent de-butylation finally leads to a compound of general formula IVa as described in the literature (Kamitori et al., Heterocycles 1994, 38, 21-25; Kamitori et al. J. Heterocycl. Chem. 1993, 30, 389-391). Another method for preparing compounds of formula IVa involves treating an aldehyde of formula Va with trichloroacetylhydrazine to get trichloroacetylhydrazone VIa which is subsequently combined with 1,3 diketone compounds of general formula VIIIa to give products of general formula IVa, as exemplified in the literature (Kaim et al., Synlett 2000, 353-355).

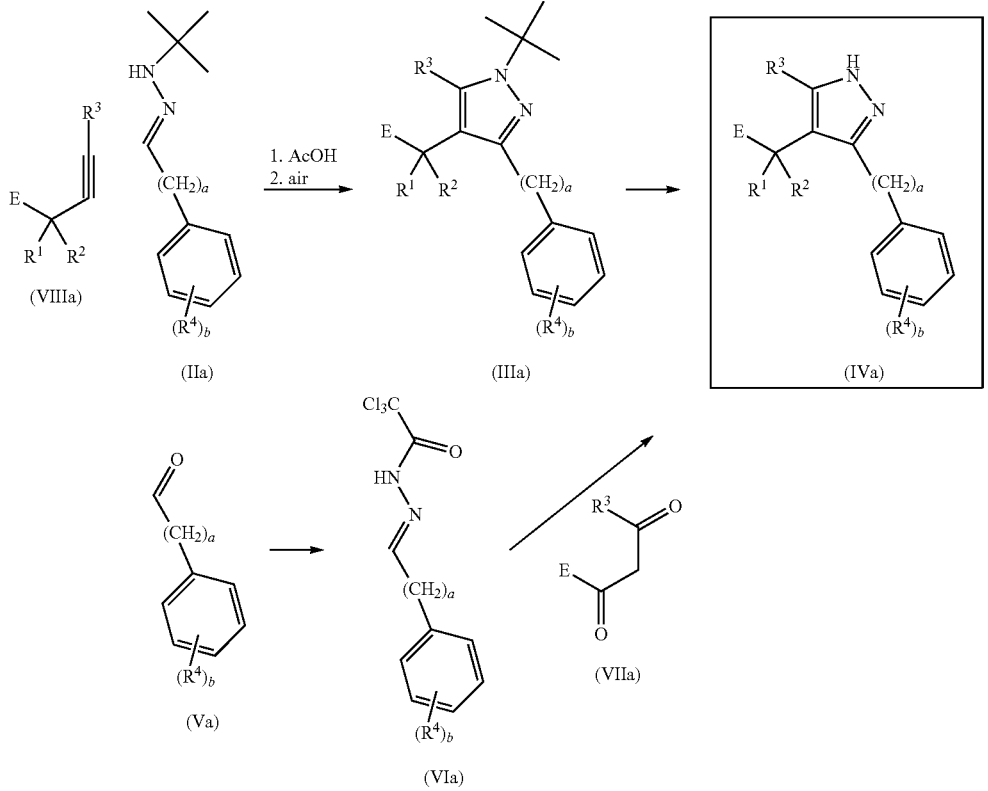

Scheme 1

$L_B$ is OH, B(OH)$_2$, B(OMe)$_2$, BF$_3^-$ or 4,4,5,5-tetramethyl-1,3,2-dioxaborolan-2-yl;

In an even more preferred synthesis method $E_L$ is chlorine or OH;

$E_N$-H is OH or NH$_2$;

$L_A$ is fluorine;

$L_B$ is OH.

In another more preferred synthesis method $E_L$ is chlorine or OH;

$E_N$-H is OH or NH$_2$;

$L_A$ is OH;

$L_B$ is halogen.

Pyrazole compounds of general formula IVa are known in the art and, to the extent not commercially available, are readily synthesized by standard procedures commonly employed in the art as illustrated in Scheme 1. In case where R$^1$ and R$^2$ are together carbonyl, pyrazole compounds of general formula IVa may be prepared by combining an acetylene compound of general formula VIIIa with a hydrazone of general formula IIa in acetic acid and in the presence of air to get t-butylatet pyrazole compound of general formula IIIa.

In Scheme 1 shown above, the variants R$^1$ to R$^3$, a and b are as defined in the claims. Isoxazole compounds of the general formula IVb are known in the art and, to the extent not commercially available, are readily synthesized by standard procedures commonly employed in the art (Scheme 2), for example by combining acetylene compound of general formula VIIIa with an alpha-chlorooxime compound of formula IIb as described by Quilio et al., Gazz. Chim. Ital. 1937, 67, 589. Alternatively, if R$^1$ and R$^2$ are together carbonyl, compounds IVb are accessible by reacting alpha-chlorooxime of formula IIb with 1,3-dicarbonyl compound Vb as described, for example, by Maloney et al., J. Med. Chem. 2000, 43(16), 2971-2974 and by Doley et al, J. Chem. Soc. 1963, 5838-5845. Another method for preparing compounds of formula IVb is especially suitable if R$^3$ is alkylamino and involves combining an acetylene compound of formula VIIIa with nitrile oxides of general formula VIb as exemplified by Himbert et al., Liebigs Ann. Chem., 1990, 4, 403-407 and in Beyer et al., Justus Liebigs Ann. Chem. 1970, 45-54.

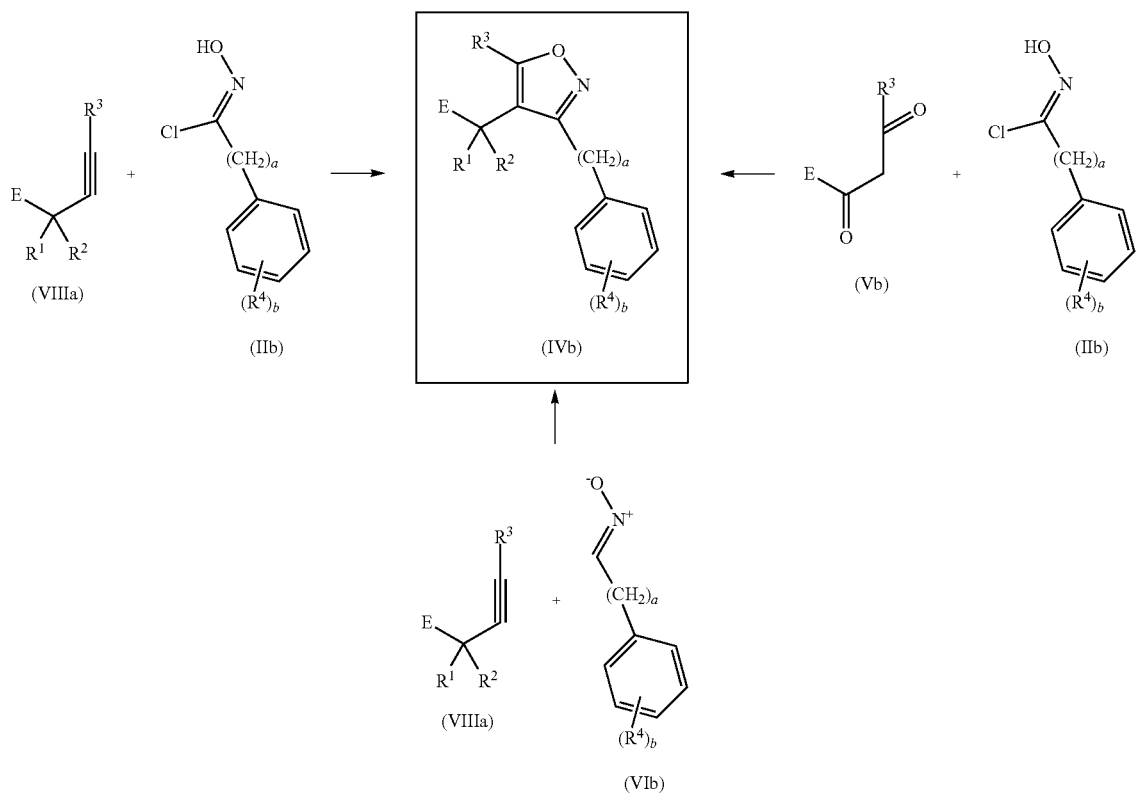

Compounds of formula IVc (Scheme 3) are known in the art and, to the extent not commercially available, readily synthesized by standard procedures commonly employed in the art, for example by the procedures described by Y. Chen et al, Heterocycles 1995, 41, 175 and B. Chantegral et al., J. Org. Chem. 1984, 49, 4419-4424. Compounds of formula IVd are known in the art and, to the extent not commercially available, readily synthesized by standard procedures commonly employed in the art, for example by the procedures described by J. Piet et al., Bull. Soc. Chim. Belg., 1996, 105(1), 33-44 and by A. Cwiklicki et al., Arch. Pharm. 2004, 337(3), 156-163. Compounds of formula IVe are known in the art and, to the extent not commercially available, are readily synthesized by standard procedures commonly employed in the art, for example by the procedures described by G. Mitchell et al, J. Chem. Soc. Perkin Trans 1, 1987, 413-422 and Y. Piterskaya et al., Russ. J. Gen. Chem. 1996, 66(7), 1150-1157.

Scheme 3

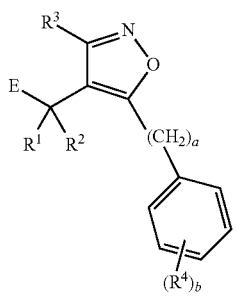

(IVc)

-continued (IVd)

(IVe)

The variants of compounds of formula IVa-IVe may optionally be further transformed into other variants of compounds of formula IVa-IVe by using derivatisation reactions known to the person skilled in the art, which are described in the literature, for example in: T. Eicher, S. Hauptmann "The Chemistry of Heterocycles; Structures, Reactions, Synthesis and Application", 2$^{nd}$ edition, Wiley-VCH 2003 (hereafter referred to as Eicher); "March's Advanced Organic Chemistry: Reactions, Mechanisms, and Structure", 5th Edition; John Wiley & Sons (hereafter referred to as March); Larock "Comprehensive Organic Transformations", VCH Publishers, New York, N.Y. 1989 (hereafter referred to as Larock); Fieser et al. "Fiesers' Reagents for organic Synthesis" John Wiley & Sons 2000 (hereafter referred to as Fieser).

Compounds of general formula XII and XIII as depicted in Scheme 4 are known in the art and, to the extent not commercially available, readily synthesized by standard procedures commonly employed in the art, for example by the procedures described by the literature cited above. Specific preparations can be found in the examples section.

Compounds of general formula IVa-IVe, IXa, IXb, XII, XIII and XIV may optionally be equipped with a temporarily attached protecting group remaining in the compound after its conversion. In later course of the synthesis sequence the protecting group is removed as taught in: T. Greene, P. Wuts "Protective groups in organic synthesis" 3$^{rd}$ ed. Wiley & Sons 1999 (hereafter referred to as Greene).

A typical synthesis for the compounds of general formula (I) involves a multistep synthesis sequence as depicted in Scheme 4 and in Scheme 5.

In step A (scheme 4), a suitable compound of general formula XII is dissolved or suspended in a suitable solvent, preferably but not limited to dimethylformamide, dimethylacetamide, tetrahydrofurane, benzene, pyridine, N-methylpyrrolidone, toluene, dichloromethane or ether and, if advantageous, a suitable base is optionally added, including but not limited to sodium methoxide, potassium methoxide, potassium carbonate, sodium hexamethyldisilazane, lithium diisopropylamide, n-butyllithium or an amine base such as diisopropylethylamine, followed by the addition of a compound of general formula XIII. If a base is required, it is typically employed in a one to one ratio. However, as the skilled artisan would appreciate, a molar excess, usually in about 1-3 fold molar excess is acceptable. The reactants are typically combined at a temperature from about 0° C. to about 200° C., preferably from 50° C. to 200° C. and the resulting mixture is typically agitated for from about 5 minutes to about 72 hours. In case where reactants XII and XIII are chosen in a way that one functional group, either $L_A$ or $L_B$, is bromine or iodine and the other functional group is OH, copper metal and a copper salt, such as CuI can be used as an activator as described in F. Ullmann et al., Ber. Dtsch. Chem. Ges. 1904, 37, 853-854. Such activators are usually employed in a 1-5 fold molar excess. Alternatively, instead of using copper compounds, a palladium catalyst system can be employed as described in: L. Buchwald et al., Angew. Chem. 2006, 118, 4427-4432. In case where reactants XII and XIII are chosen in a way that one functional group, either $L_A$ or $L_B$, is chlorine, bromine or iodine and the other functional group is B(OH)$_2$, B(OMe)$_2$, BF$_3^-$ or 4,4,5,5-tetramethyl-1,3,2-dioxaborolan-2-yl, addition of a copper species is necessary as described in Chan et al., Tetrahedron Letters 2003, 44, 3863-3865. In a preferred case, where $L_A$ is fluorine and $L_B$ is OH, a high boiling solvent such as dimethyl acetamide or N-methyl pyrrolidone or hexamethyl phosphorous triamide is especially suitable and an inorganic base such as potassium carbonate is used. Reaction temperatures range from 100-200° C. and the reaction rate can be further increased using microwave irradiation.

In another preferred case, when $L_A$ is OH and $L_B$ is bromine, pyridine is preferred as a solvent, copper powder und CuI are used together as additives.

The starting materials and products of step A may optionally be equipped with a protecting group remaining in the compound which needs to be removed in an additional step as taught in Greene.

In an optional step B1 or B2, the variants of compounds of formula XIV may optionally be further transformed into other variants of compounds of formula IXa and IXb by using derivatisation reactions known to the person skilled in the art, which are described in Greene, Either and Larock. Such derivatisation reactions are thought to turn a functional group E in formula XIV into a functional group moiety $E_N$-H in formula IXa or into a functional group $E_L$ in formula IXb, respectively. General methods for functional group interconversions are described in Larock. In one example of step B1, E is a nitro group, which is reduced into an amino group $E_N$-H. In one example of step B2, E is a nitro group, which is converted into a bromine $E_L$ by reduction, subsequent diazotation and subsequent substitution by a bromide. In another example of step B2, E is a hydrogen which is turned into a chlorine by a chlorination step.

The starting materials and products of step B may optionally be equipped with a protecting group remaining in the compound which needs to be removed in an additional step as taught in Greene.

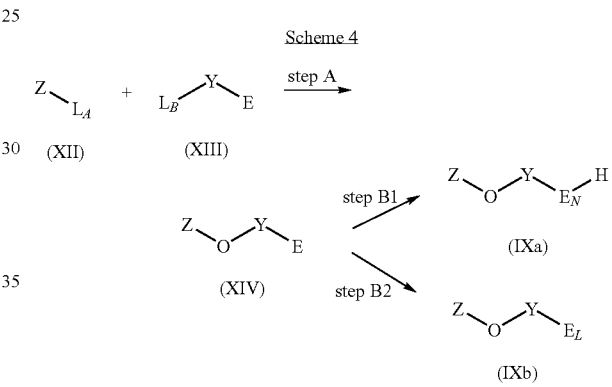

In steps C1 (scheme 5), a suitable compound of general formula IXa, equipped with a nucleophilic group chosen from $E_N$-H, is dissolved or suspended in a suitable solvent, preferably but not limited to dimethylformamide, tetrahydrofurane, benzene, toluene, dichloromethane or ether and, if advantageous, a suitable base is optionally added, including but not limited to sodium methoxide, potassium methoxide, potassium carbonate, sodium hexamethyldisilazane, lithium dilsopropylamide, n-butyllithium or an amine base such as diisopropylethylamine, followed by the addition of a compound of general formula IVa-IVe, equipped with a suitable leaving group $E_L$. If a base is required, it is typically employed in a one to one ratio. However, as the skilled artisan would appreciate, a molar excess, usually in about 1-3 fold molar excess is acceptable. The reactants are typically combined at a temperature from about 0° C. to about 100° C., preferably at room temperature and the resulting mixture is typically agitated for from about 5 minutes to about 48 hours. In case where $E_L$ is a poor leaving group (OH for example), it needs to be activated by adding activating reagents to the reaction mixture such as MeSO$_2$Cl, CF$_3$(SO$_2$)$_2$O or Mitsunobu reagents diisopropyldiazenedicarboxylate and triphenylphosphine, for example, as shown in example 1.

Preferably, in step C1 the leaving group $E_L$ in compound of formulas IVa to IVe is chlorine or OH. Most preferably, the nucleophilic group $E_N$-H in compounds of general formula IXa is OH.

In case where $E_N$-H is OH and $E_L$ is chlorine, the reactants of general formula IXa are dissolved or suspended in a suitable solvent, preferably tetrahydrofurane, DMF or methanol and typically 1-2 equivalent of a suitable base, such as sodium hydride or sodium methanolate are added. Subsequently a compound of general formula IVa-IVe is added and the resulting mixture is typically agitated for from about 5 minutes to about 48 hours. Reaction temperatures may range from −10° C. to +60° C., typically from −10° C. to +10° C. In case where $E_N$-H is OH and $E_L$ is also OH, the reactants of general formula IVa-IVe and IXa are dissolved or suspended in a suitable solvent, preferably benzene or toluene, and 1 to 2 equivalents triphenylphosphine and diisopropyldiazenedicarboxylate (DEAD) are added without addition of a base. The reactants are typically combined at a temperature from about 0° C. to about 50° C., preferably at room temperature. The reaction times are typically 1 h to 12 h. The solvents are usually removed by distillation at temperatures typically ranging from 10 to 50° C. The crude product is optionally purified by column chromatography and other purification methods known in the art.

In step C2, a suitable compound of general formula IXb, equipped with a suitable leaving group $E_L$, is combined with a compound of general formula IVa-IVe, equipped with an nucleophilic group chosen from $E_N$-H under similar conditions as applied in step C1.

Most preferably, in step C2 the leaving group $E_L$ in compound of general formula IXb is chlorine and the nucleophilic group $E_N$-H in compounds of general formula IVa-IVe is OH or $NH_2$. In such cases the reactants of general formula IVa-IVe are dissolved or suspended in a suitable solvent, preferably tetrahydrofurane, DMF or methanol and typically 1-2 equivalents of a suitable base, such as sodium hydride or sodium methanolate are added. Subsequently a compound of general formula IXb is added and the resulting mixture is typically agitated for about 1 h to 12 h. Reaction temperatures may range from −10° C. to +60° C., typically from −10° C. to +10° C.

The starting materials and products of step C1 and step C2 may optionally be equipped with a protecting group remaining in the compound which needs to be removed in an additional step as taught in Greene.

The variants of compounds of general formula I may optionally be further transformed into other variants of compounds of general formula I by using derivatisation reactions known to the person skilled in the art, which are described in Greene, Eicher and Larock. Specific examples of such functional group interconversions can be found in the examples section.

Scheme 5

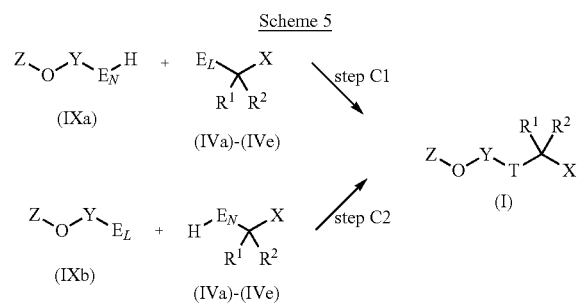

The skilled artisan will appreciate, that the synthesis steps described above may be optionally carried out in an alternative synthesis sequence, i.e. a compound of general formula IVa to IVe may be combined with a compound of general formula XIII by the techniques mentioned above and the resulting intermediate is subsequently combined with a compound of general formula XII to give products of general formula (I). The particular order of steps required to produce the compounds of formula I is dependent upon the particular compound being synthesized, the starting compound, and the relative lability of the substituted moieties.

Most preferred examples of the synthesis procedures are outlined in Scheme 6 where
$R^3$ is alkyl or dialkylamino;
$R^4$ is halogen;
b=2;
E is H, chlorine, OMe or OH;
$L_A$ is OH or fluorine;
$L_B$ is bromine or OH;
Y is $Y^1$, $Y^3$ or $Y^5$;
$R^8$ is $CH_3$ or $CF_3$;
c=1;
Z is phenyl-A-$R^9$ or pyridyl-A-$R^9$;
A is a bond or —$CH_2$—;
$R^9$ is COOH or COOMe.

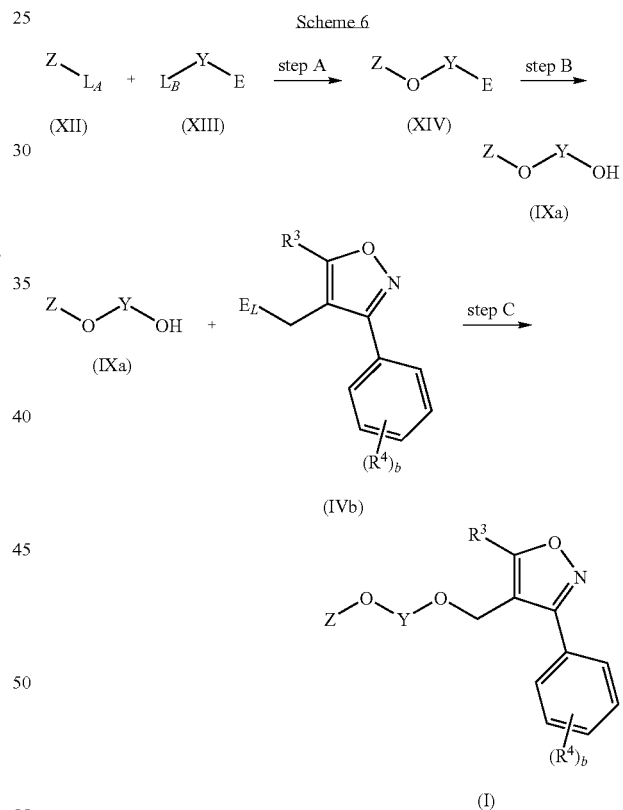

Step A of most preferred embodiments is as described above.

In step B of most preferred embodiments, a substituent E is interconverted into a hydroxyl group. In one embodiment, a methoxy group is converted into a hydroxyl by treatment with a lewis acid, such as iodotrimethylsilane or boron tribromide. In another embodiment where Y is $Y^1$ and E is hydrogen, E is converted into a chlorine by N-oxidation of the $Y^1$ pyridine and subsequent treatment with thionyl chloride.

In step C of most preferred embodiments of the invention, a suitable compound of general formula (IVb) is dissolved or suspended in a suitable solvent, preferably tetrahydrofurane, methanol, benzene or toluene. If $E_L$ is chlorine, a base is added, for example sodium hydride or sodium methanolate or the like. In case where $E_L$ is OH, 1 to 2 equivalents triphenylphosphine and diisopropyldiazenedicarboxylate (DIAD) are added instead of a base. A compound of general formula IXa is added and the reactants are typically combined at a temperature ranging from about 0° C. to about 50° C., preferably at room temperature. The reaction times are typically 1 to 24 h. The solvents are usually removed by distillation at temperatures typically ranging from 10° C. to 50° C. The crude product of general formula I is optionally purified by extraction methods and/or column chromatography and other purification methods known in the art.

As mentioned above, compounds of general structure I may further be converted into other variants of the same general structure by single or multistep functional group interconversions such as described in Larock.

In most preferred embodiments, a carboxylic ester group in compound of formula I is saponified to give the corresponding carboxylic acid of formula I. In a typical procedure, compound of formula I is dissolved in an suitable solvent, such as an alcohol or an ether, preferably methanol, optionally containing 0-50% of water, together with 1 to 10 equivalents, preferably 1 to 2 equivalents of a base, preferably NaOH or LiOH. The reactants are typically combined at a temperature from about 0° C. to about 80° C., preferably from room temperature to 60° C., until sufficient conversion is detected by methods known in the art, such as TLC or HPLC. The reaction times typically range from 1 to 24 h. The crude product of general formula I is optionally purified by extraction methods and/or column chromatography and other purification methods known in the art.

Unless otherwise noted, all non-aqueous reactions were carried out either under an argon or nitrogen atmosphere using commercial dry solvents. Compounds were purified by flash column chromatography using silica gel 60 (230-400 mesh), or by reverse phase preparative HPLC using conditions as described in the synthesis procedure. LC/MS analysis was done using a Surveyor MSQ (Thermo Finnigan, USA) with APCI ionization, column: Waters XTerra MS C18 3.5 μm 2.1×30 mm, injection volume 1 μl, flow rate 1.0 ml/min, mobile phase: A—0.1% formic acid; B—acetonitrile.

| Gradient table: | | |
|---|---|---|
| time, min. | A % | B % |
| 0.0 | 100 | 0 |
| 0.1 | 100 | 0 |
| 3.0 | 5 | 95 |
| 3.8 | 5 | 95 |
| 3.9 | 100 | 0 |
| 6.5 | 100 | 0 |

Detection: diode array (PDA), 190-800 nm; masspec (APCI+ or −). $^1$H NMR spectra were recorded on a Varian MERCURY plus 400 MHz spectrometer. Chemical shift values are given in ppm relative to tetramethylsilane (TMS), with the residual solvent proton resonance as internal standard. Melting points were taken on a Sanyo Gallenkamp melting point apparatus (MPD350.BM3.5).

EXAMPLE 1

4-(6-((3-(2,6-Dichlorophenyl)-5-isopropylisoxazol-4-yl)methoxy)pyridin-3-yloxy)benzoic acid

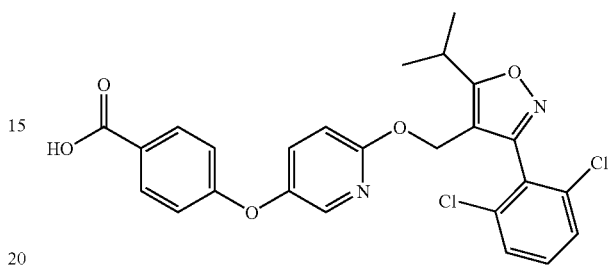

Step 1

A suspension of 5-bromo-2-methoxy-pyridine (5.9 g, 30 mmol), methyl 4-hydroxy-benzoate (4.0 g, 26 mmol), $K_2CO_3$ (4.7 g, 34 mmol), Cu powder (0.25 g, 4 mmol) and CuI (0.25 g, 1.3 mmol) in pyridine (25 ml) was refluxed for 10 h and allowed to cool to room temperature. The resulting mixture was poured in 100 g of crushed ice, neutralized with HCl to pH 7.5 and extracted with diethyl ether. The extract was evaporated in vacuo, the residue was separated by column chromatography on silica (eluent hexanes-ethyl acetate 8:1) to give 2.8 g (35%) of 4-(6-methoxy-pyridin-3-yloxy)-benzoic acid methyl ester as colorless oil.

Step 2

To a solution of 4-(6-methoxy-pyridin-3-yloxy)-benzoic acid methyl ester (0.2 g, 0.8 mmol) in acetonitrile (6 ml) was added iodotrimethylsilane (0.346 g, 1.73 mmol) and the mixture was allowed to reflux for 1 h. The reaction mixture was diluted with water (8 ml) and extracted with chloroform. The extract was washed with 10% aqueous $Na_2S_2O_3$ and water and dried over anhydrous $Na_2SO_4$. The solvent was removed under reduced pressure to afford 0.19 g (87%) of 4-(6-hydroxy-pyridin-3-yloxy)-benzoic acid methyl ester as yellowish crystals.

Step 3

To a suspension of 4-(6-hydroxy-pyridin-3-yloxy)-benzoic acid methyl ester (0.084 g, 0.34 mmol) was added [3-(2,6-dichloro-phenyl)-5-isopropyl-isoxazol-4-0]-methanol (0.098 g, 0.34 mmol) and triphenylphosphine (0.107 g, 0.41 mmol) in benzene (6 ml) followed by dropwise addition of diisopropyldiazenedicarboxylate (0.089 g, 0.44 mmol). The reaction mixture was allowed to stir at room temperature for 8 h was subsequently concentrated under reduced pressure. The residue was separated by reversed phase HPLC (column Reprosil-Pur C18-A9, 250×20 mm, gradient elution acetonitrile:water (2:1)—pure acetonitrile) to give 0.076 g (44%) of 4-{6-[3-(2,6-dichloro-phenyl)-5-isopropyl-isoxazol-4-ylmethoxy]-pyridin-3-yloxy}-benzoic acid methyl ester as colorless oil.

Step 4

To a solution of 4-{6-[3-(2,6-dichloro-phenyl)-5-isopropyl-isoxazol-4-ylmethoxy]-pyridin-3-yloxy}-benzoic acid methyl ester (0.070 g, 0.14 mmol) in methanol (5 ml) was added NaOH (0.104 g, 2.6 mmol) and water (0.25 ml) and the reaction mixture was stirred at room temperature for 30 h. Then solvent was evaporated, water (1.5 ml) was added and the mixture was acidified to pH 6 with 1N hydrochloric acid and the resulting solution was extracted with ethyl acetate. The extract was dried over anhydrous Na$_2$SO$_4$ and the solvent was removed under reduced pressure to afford 4-{6-[3-(2,6-dichloro-phenyl)-5-isopropyl-isoxazol-4-ylmethoxy]-pyridin-3-yloxy}-benzoic acid as colorless oil. Yield: 0.037 g (53%).

$^1$H-NMR (400 MHz, DMSO-d$_6$); δ (ppm) 1.35 (6H, d), 3.50 (1H, sept), 5.10 (2H, s), 6.64 (1H, d), 6.93 (2H, d), 7.44-7.60 (4H, m), 7.81 (1H, d), 7.90 (2H, d).

LC-MS: rt 3.54 min; m/z [M+H]$^+$ 498.8 (calculated: 499.1).

EXAMPLE 2

3-(6-((3-(2,6-Dichlorophenyl)-5-isopropylisoxazol-4-yl)methoxy)pyridin-3-yloxy)benzoic acid

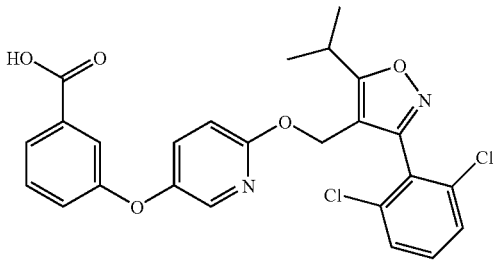

Step 1

A suspension of 5-bromo-2-methoxy-pyridine (5.4 g, 29 mmol), ethyl 3-hydroxybenzoate (4.0 g, 24 mmol), K$_2$CO$_3$ (4.3 g, 30 mmol), Cu powder (0.30 g, 4.8 mmol) and CuI (0.30 g, 1.56 mmol) in pyridine (25 ml) was refluxed for 18 h. The resulting mixture was mixed with 100 g of crushed ice, neutralized with 1N hydrochloric acid to pH 7.5 and extracted with ether. The extract was evaporated in vacuo, the obtained crude product was purified by column chromatography on silica (eluent hexanes-ethyl acetate 8:1) to afford 1.55 g (20%) of 3-(6-methoxy-pyridin-3-yloxy)-benzoic acid ethyl ester as colorless oil.

Step 2

A solution of 3-(6-methoxy-pyridin-3-yloxy)-benzoic acid ethyl ester (0.5 g, 1.83 mmol) in acetonitrile (8 ml) and iodotrimethylsilane (0.439 g, 2.2 mmol) was refluxed for 1 h, the mixture was diluted with water (8 ml) and extracted with chloroform. The extract was washed with 10% of aqueous Na$_2$S$_2$O$_3$, water, dried over anhydrous Na$_2$SO$_4$ and the solvent was removed under reduced pressure to afford 0.327 g (69%) of 3-(6-hydroxy-pyridin-3-yloxy)-benzoic acid ethyl ester as colorless powder.

Step 3

To a suspension of 3-(6-hydroxy-pyridin-3-yloxy)-benzoic acid ethyl ester (0.20 g, 0.77 mmol), [3-(2,6-dichloro-phenyl)-5-isopropyl-isoxazol-4-yl]-methanol (0.22 g, 0.77 mmol), triphenylphosphine (0.242 g, 0.92 mmol) in benzene (10 ml) was added dropwise diisopropyldiazenedicarboxylate (0.202 g, 1.00 mmol). The reaction mixture was stirred at room temperature for 4 h and concentrated under reduced pressure. The resulting residue was further purified by column chromatography using silica (eluent hexanes-ethyl acetate 5:1) to give 0.167 g (41%) of 3-{6-[3-(2,6-dichloro-phenyl)-5-isopropyl-isoxazol-4-ylmethoxy]-pyridin-3-yloxy}-benzoic acid ethyl ester as colorless oil.

Step 4

NaOH (0.228 g, 5.7 mmol) in water (0.25 ml) was added to a solution of 3-{6-[3-(2,6-dichloro-phenyl)-5-isopropyl-isoxazol-4-ylmethoxy]-pyridin-3-yloxy}-benzoic acid ethyl ester (0.157 g, 0.3 mmol) in ethanol (5 ml) and the reaction mixture was stirred at room temperature for 50 h. The solvent was removed under reduced pressure and the residue diluted with water (1.5 ml) and acidified to pH 6. The resulting solution was extracted with ethyl acetate and the extract was dried over anhydrous Na$_2$SO$_4$. The solvent was removed under reduced pressure to afford 3-{6-[3-(2,6-dichloro-phenyl)-5-isopropyl-isoxazol-4-ylmethoxy]-pyridin-3-yloxy}-benzoic acid as colorless oil. Yield 0.14 g (33%).

$^1$H-NMR (400 MHz, DMSO-d$_6$); δ (ppm) 1.35 (6H, d), 3.53 (1H, sept), 5.12 (2H, s), 6.64 (1H, dd), 7.35 (1H, s), 7.43-7.61 (5H, m), 7.67 (1H, d), 7.80 (1H, d).

LC-MS: rt 3.55 min; m/z [M+H]$^+$ 498.8 (calculated: 499.1).

EXAMPLE 3

4-(5-((3-(2,6-Dichlorophenyl)-5-isopropylisoxazol-4-yl)methoxy)-3-methylpyridin-2-yloxy)benzoic acid

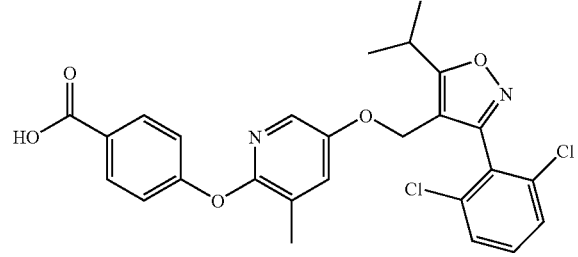

Step 1

A mixture of commercial 2-chloro-3-methyl-5-nitro-pyridine (0.5 g, 2.88 mmol), 4-hydroxy-benzoic acid methyl ester (0.45 g, 2.96 mmol) and K$_2$CO$_3$ (0.398 g, 2.90 mmol) in anhydrous acetone (20 ml) was refluxed for 15 h. After cooling to room temperature, the precipitate was filtered and washed with acetone (2×10 ml). The filtrates were concentrated at reduced pressure and the residue was purified by column chromatography (eluting with DCM/hexane 5:1 then DCM) to provide methyl 4-(3-methyl-5-nitropyridin-2-yloxy)benzoate (0.788 g, 95% yield).

Step 2

To a mixture of 4-(3-methyl-5-nitro-pyridin-2-yloxy)-benzoic acid methyl ester (0.43 g, 1.49 mmol) from the previous step and zinc dust (0.932 g, 14.2 mmol) in methanol (15 ml) was added dropwise acetic acid (0.32 ml, 5.12 mmol). The mixture was stirred for 1 h at room temperature and filtered through a thin silica pad to remove inorganics. The filtrate was concentrated at reduced pressure to dryness to provide methyl 4-(5-amino-3-methylpyridin-2-yloxy)benzoate (0.346 g, 90% yield).

Step 3

To a 0-5° C. solution of NaNO$_2$ (0.039 g, 0.55 mmol) in sulfuric acid (0.66 ml) was added in small portions a solution of 5-amino-3-methyl-pyridin-2-yloxy)-benzoic acid methyl ester (0.13 g, 0.5 mmol) in acetic acid (1.5 ml). The reaction mixture was stirred at room temperature for 1 h and then poured dropwise into 50 ml of boiling water. The cooled solution was extracted with diethyl ether (20 ml) and dichloromethane (2×10 ml). The combined organic extracts were dried over $Na_2SO_4$ and the solvents were removed in vacuo. The residue was purified by preparative HPLC to provide methyl 4-(5-hydroxy-3-methylpyridin-2-yloxy)benzoate (0.042 g, 32% yield).

Cl MS m/z 260.11 (MH+).

Step 4

To a suspension of methyl 4-(5-hydroxy-3-methylpyridin-2-yloxy)benzoate synthesised in step 3 (0.042 g, 0.162 mmol), [3-(2,6-dichloro-phenyl)-5-isopropyl-isoxazol-4-yl]methanol (0.046 g; 0.162 mmol) (for preparation refer to: P. Maloney et al. "Identification of a chemical tool for the orphan nuclear receptor FXR" J. Med. Chem. 2000, 43(16), 2971-2974) and triphenylphosphine (0.052 g, 0.2 mmol) in benzene (2 ml) was added diisopropyl azodicarboxylate (0.051 g, 0.25 mmol). The mixture was stirred at room temperature for 20 h, the solvent was removed in vacuo and the residue was purified by preparative HPLC to provide methyl 4-(5-((3-(2,6-dichlorophenyl)-5-isopropylisoxazol-4-yl)methoxy)-3-methylpyridin-2-yloxy)benzoate (0.06 g, 70% yield).

Step 5

To a solution of the product derived from the previous step (0.06 g, 0.13 mmol) in methanol (4 ml) was added a solution of NaOH (0.012 g, 0.29 mmol) in water (1 ml). The mixture was stirred at room temperature for 16 h and at 50° C. for additional 8 h. The solvent was removed in vacuo, the residue was redissolved in water and the resulting solution was acidified with 2N HCl to pH 5. The formed precipitate was collected by filtration, washed with water and dried to provide a crude product. Purification by column chromatography (silica column, eluent: chloroform/methanol 40:1 to 10:1) afforded 4-(5-((3-(2,6-dichlorophenyl)-5-isopropylisoxazol-4-yl)methoxy)-3-methylpyridin-2-yloxy)benzoic acid (0.027 g, 47% yield).

M.p. 74-76° C.

$^1$H-NMR (300 MHz, $CDCl_3$); δ (ppm) 1.40 (6H, d), 2.20 (3H, s), 3.31 (1H, sept.), 4.78 (2H, s), 7.00-7.08 (3H, m), 7.30-7.45 (3H, m), 7.60 (1H, d), 8.05-8.10 (2H, d).

LC-MS: rt 2.05 min; m/z $[M+H]^+$ 513.1 (calculated: 513.1).

EXAMPLE 4

4-(6-((3-(2,6-Dichlorophenyl)-5-isopropylisoxazol-4-yl)methoxy)pyridin-3-yloxy)-N-(methylsulfonyl)benzamide

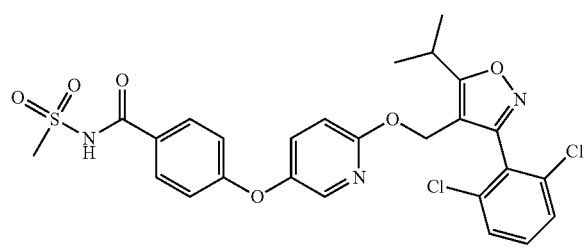

4-N,N-Dimethylaminopyridine (0.062 g, 0.65 mmol), (3-dimethylamino-propyl)-ethyl-carbodiimide hydrochloride (0.098 g, 0.51 mmol) and triethylamine (0.062 g, 0.65 mmol) were added to a solution of the compound from example 1 (4-{6-[3-(2,6-dichloro-phenyl)-5-isopropyl-isoxazol-4-ylmethoxy]-pyridin-3-yloxy}-benzoic acid) (0.125 g, 0.25 mmol) in dry dichloromethane (5 ml). The reaction mixture was stirred for 15 h at room temperature. The reaction mixture was evaporated, the residue was dissolved in ethyl acetate, the solution was washed with brine, 1N HCl, brine, dried over sodium sulfate and evaporated. The residue was triturated with diethyl ether-hexane mixture to give the title product as a colorless solid, yield: 0.105 g (73%).

M.p. 182-184° C.

$^1$H-NMR (400 MHz, DMSO-$D_6$); δ (ppm) 1.34 (6H, d), 3.31 (3H, s), 3.43-3.58 (1H, m), 5.12 (2H, s), 6.67 (1H, d), 6.98 (2H, d), 7.45-7.61 (4H, m), 7.82 (1H, s), 7.94 (2H, d), 11.92 (1H, br. s).

LC-MS: rt 2.03 min; m/z $[M+H]^+$ 576.2 (calculated: 576.1).

EXAMPLE 5

4-(6-((3-(2,6-Dichlorophenyl)-5-isopropylisoxazol-4-yl)methoxy)pyridazin-3-yloxy)benzoic acid

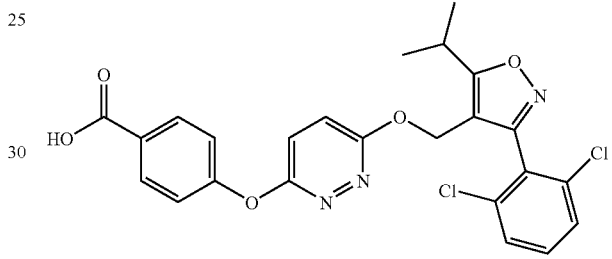

Step 1

Potassium tert-butoxide (0.87 g, 7.75 mmol) was added in portions to a solution of 4-hydroxybenzoic acid methyl ester 1 (1.15 g, 7.56 mmol) in anhydrous THF (25 ml). The mixture was stirred at room temperature for 30 minutes, then 3,6-dichloro-pyridazine (1.12 g, 7.56 mmol) was added. The reaction mixture was stirred at room temperature for 1 h and heated at reflux for 14 h. The mixture was cooled to room temperature and diluted with water (100 ml). The formed precipitate was collected by filtration, washed with water and dried to obtain 1.315 g (66%) of 4-(6-chloro-pyridazin-3-yloxy)-benzoic acid methyl ester which was used for the next step without further purification.

Cl MS m/z 265 $[M+H]^+$

Step 2

A mixture of 4-(6-chloro-pyridazin-3-yloxy)-benzoic acid methyl ester (1.0 g, 3.78 mmol) from the previous step and anhydrous potassium acetate (0.526 g, 5.37 mmol) in glacial acetic acid (10 ml) was refluxed for 13 h. The volatiles were evaporated in vacuo and the residue was diluted with dichloromethane (20 ml). The separated solid was collected by filtration, washed with 50% aqueous ethanol (2×5 ml) and water (4×7 ml) and dried to provide 0.7 g (43%) of 4-(6-oxo-1,6-dihydro-pyridazin-3-yloxy)-benzoic acid methyl ester.

Cl MS m/z 247 $[M+H]^+$

Step 3

To a mixture of 4-(6-oxo-1,6-dihydro-pyridazin-3-yloxy)-benzoic acid methyl ester (0.43 g, 1.75 mmol), [3-(2,6-dichloro-phenyl)-5-isopropyl-isoxazol-4-yl]-methanol (0.50 g, 1.75 mmol) and triphenylphosphine (0.56 g, 2.1 mmol) in benzene (12 ml) was added dropwise 0.6 ml (2.9 mmol) of diisopropyl 1,2-diazenedicarboxylate (DIAD). The reaction mixture was stirred at room temperature for 27 h and the solvent was removed in vacuo. The residue was subjected to preparative HPLC purification eluting with acetonitrile/water 1:1 to provide 0.08 g (9%) of the desired 4-{6-[3-(2,6-dichloro-phenyl)-5-isopropyl-isoxazol-4-ylmethoxy]-pyridazin-3-yloxy}-benzoic acid methyl ester together with 0.52 g (58%) of 4-{1-[3-(2,6-dichloro-phenyl)-5-isopropyl-isoxazol-4-ylmethyl]-6-oxo-1,6-dihydro-pyridazin-3-yloxy}-benzoic acid methyl ester.

Cl MS m/z 514 [M+H]$^+$

Step 4

To a suspension of 4-{6-[3-(2,6-dichloro-phenyl)-5-isopropyl-isoxazol-4-ylmethoxy]-pyridazin-3-yloxy}-benzoic acid methyl ester from the previous step (0.083 g, 0.155 mmol) in ethanol (5 ml) was added sodium hydroxide (0.02 g, 0.5 mmol) and water (0.2 ml). The reaction mixture was stirred at room temperature for 20 h. The volatiles were removed in vacuo and the residue was diluted with water (3 ml) and the resulting solution was acidified to pH 5 by addition of 4N HCl. The formed precipitate was collected by filtration, washed with water (3×5 ml) and dried on air to provide 0.08 g (99%) of the title product.

$^1$H-NMR (400 MHz, DMSO-d$_6$); δ (ppm) 1.31 (6H, d), 3.41-3.57 (1H, m), 5.21 (2H, s), 7.09 (1H, d), 7.20 (2H, d), 7.41 (1H, d), 7.47-7.61 (3H, m), 7.96 (2H, d), 12.80 (1H, br. s).

Cl MS mlz 500 [M+H]$^+$

FRET Activity Assay

Determination of a ligand mediated cofactor peptide interaction to quantify ligand binding to the nuclear receptor Farnesoid X Receptor (FXR) was performed as follows:

Preparation of human farnesoid X receptor (FXR) alpha ligand binding domain: The human FXRalpha ligand binding domain (LBD) was expressed in E. coli strain BL21(DE3) as an N-terminally glutathione-S-transferase (GST) tagged fusion protein. The DNA encoding the FXR ligand binding domain was cloned into vector pDEST15 (Invitrogen). Expression was under control of an IPTG inducible T7 promoter. The amino acid boundaries of the ligand binding domain were amino acids 187-472 of Database entry NM_005123 (RefSeq). Expression and purification of the FXR-LBD: An overnight preculture of a transformed E. coli strain was diluted 1:20 in LB-Ampicillin medium and grown at 30° C. to an optical density of OD600=0.4-0.6. Gene expression was then induced by addition of 0.5 mM IPTG. Cells were incubated an additional 6 h at 30° C., 180 rpm. Cells were collected by centrifugation (7000×g, 7 min, room temperature). Per liter of original cell culture, cells were resuspended in 10 ml lysis buffer (50 mM Glucose, 50 mM Tris pH 7.9, 1 mM EDTA and 4 mg/ml lysozyme) and left on ice for 30 min. Cells were then subjected to sonication and cell debris removed via centrifugation (22000×g, 30 min, 4° C.). Per 10 ml of supernatant 0.5 ml prewashed Glutathione 4B sepharose slurry (Qiagen) was added and the suspension kept slowly rotating for 1 h at 4° C. Glutathione 4B sepharose beads were pelleted by centrifugation (2000 g, 15 sec, 4° C.) and washed twice in wash buffer (25 mM Tris, 50 mM KCl, 4 mM MgCl$_2$ and 1 M NaCl). The pellet was resuspended in 3 ml elution buffer per liter of original culture (elution buffer: 20 mM Tris, 60 mM KCl, 5 mM MgCl$_2$ and 80 mM glutathione added immediately prior to use as powder). The suspension was left rotating for 15 min at 4° C., the beads pelleted and eluted again with half the volume of elution buffer than the first time. The eluates were pooled and dialysed overnight in 20 mM Hepes buffer (pH 7.5) containing 60 mM KCl, 5 mM MgCl$_2$ as well as 1 mM dithiothreitol and 10% (v/v) glycerol. The protein was analysed by SDS-Page.

The method measures the ability of putative ligands to modulate the interaction between the purified bacterial expressed FXR ligand binding domain (LBD) and a synthetic biotinylated peptide based on residues 676-700 of SRC-1 (LCD2, 676-700). The sequence of the peptide used was B-CPSSHSSLTERHKILHRLLQEGSPS-COOH where the N-terminus was biotinylated (B). The ligand binding domain (LBD) of FXR was expressed as fusion protein with GST in BL-21 cells using the vector pDEST15. Cells were lysed by sonication, and the fusion proteins purified over glutathione sepharose (Pharmacia) according to the manufacturers instructions. For screening of compounds for their influence on the FXR-peptide interaction, the Perkin Elmer LANCE technology was applied. This method relies on the binding dependent energy transfer from a donor to an acceptor fluorophor attached to the binding partner of interest. For ease of handling and reduction of background from compound fluorescence LANCE technology makes use of generic fluorophore labels and time resolved detection Assays were done in a final volume of 25 µl in a 384 well plate, in a Tris-based buffer (20 mM Tris-HCl pH 7.5; 60 mM KCl, 5 mM MgCl$_2$; 35 ng/µl BSA), containing 20-60 ng/well recombinantly expressed FXR-LBD fused to GST, 200-600 nM N-terminally biotinylated peptide, representing SRC1 aminoacids 676-700, 200 ng/well Streptavidin-xIAPC conjugate (Prozyme) and 6-10 ng/well Eu W1024-antiGST (Perkin Elmer). DMSO content of the samples was kept at 1%. After generation of the assay mix and diluting the potentially FXR modulating ligands, the assay was equilibrated for one hour in the dark at room temperature in FIA-plates black 384 well (Greiner). The LANCE signal was detected by a Perkin Elmer VICTOR2V™ Multilabel Counter The results were visualized by plotting the ratio between the emitted light at 665 nm and 615 nm. A basal level of FXR-peptide formation is observed in the absence of added ligand. Ligands that promote the complex formation induce a concentration-dependent increase in time-resolved fluorescent signal. Compounds which bind equally well to both monomeric FXR and to the FXR-peptide complex would be expected to give no change in signal, whereas ligands which bind preferentially to the monomeric receptor would be expected to induce a concentration-dependent decrease in the observed signal.

To assess the potential of the compounds, EC50-values were determined. The following compounds shown in Table 1 exemplify such activity with "+" meaning 1 µM<EC50≦10 µM and "++" EC50≦1 µM

TABLE 1

| Example No | FRET activity |
|---|---|
| Example 1 | ++ |
| Example 2 | ++ |
| Example 3 | ++ |
| Example 4 | ++ |
| Example 5 | ++ |

Physicochemical & ADME Assays

Physicochemical and ADME parameters of examples of the present invention were determined and compared to those determined for FXR-modulating compounds A and B shown below which are state of the art and not part of the present invention.

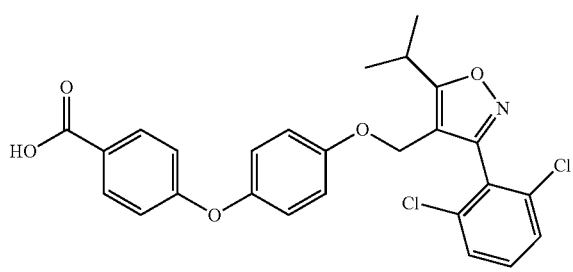

Compound A exemplified in WO03015771 and U.S. Pat. No. 7,034,046 B2

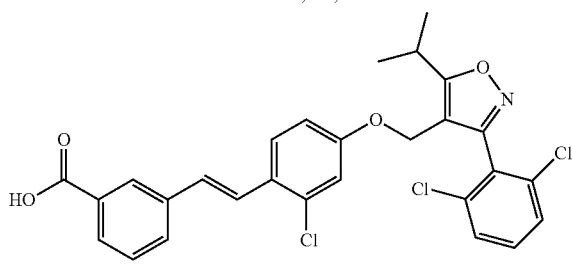

Compound B exemplified in WO0037077

Aqueous Solubility Assay

Aqueous solubility of compounds was determined by nephelometry or by shake-flask method as follows:

Protocol A, Nephelometry Method:

Solubility of compounds was measured in PBS (pH 7.4), 5% DMSO at 23° C. Nepheloskan Ascent (Thermo Electron Corporation) nephelometer was used for measurement of light scattering. Tested compounds were dissolved in DMSO to 10 mM. Prior to measurement the compounds were further diluted with PBS in the wells to final compound concentrations of 100, 70, 50, 35, 25, 17, 12 and <10 µg/ml.

The plates were incubated at room temperature for 24 hours to reach equilibrium and the scattered light was measured. Assay validation: Aqueous solubility of acetylsalicylic acid was determined to validate the assay. It was found to be >100 µg/ml at the day of experiment, which corresponds to the reported literature value of at least 2.17 mg/ml (The Merck index, 10th edition). Aqueous solubilities of examples and reference compounds are listed below in Table 2.

TABLE 2

| Compound | Aqueous solubility pH 7.4 (µM) nephelometry method |
| --- | --- |
| Compound A | 24 |
| Example 1 | >200 |

Protocol B, Shake-Flask Method:

Sample preparation: Sample and standard solution preparation is performed by mixing equal volumes of acetonitrile containing the internal standard (1 µM final concentration) with sample and calibration standard solutions (100 µl). After vigorously shaking (10 seconds) the samples are centrifuged (6000 g) for 5 minutes at 20° C. Aliquots of the particle-free supernatants are transferred to 200 µl sample vials and subsequently subjected to LC-MS/MS analysis. Assay procedure: Test concentration was 100 µM in 10 mM PBS buffer pH 7.4 with a final MeOH concentration of 1%. The volume of the incubation solution was 500 µl. Depending on each compound's solubility in MeOH, the stock concentration and the incubation concentration was adapted. The test solutions in quadruplicates were shaken at 300 rpm over a 20 hours period at room temperature, followed by centrifugation at 20000 g for 30 minutes to separate the solid phase. 100 µl of particle free sample are added to 100 µl acetonitrile containing the internal standard. The aqueous solubility of the compounds was determined by measuring the concentration of the PBS buffer supernatant by HPLC-MS/MS. Aqueous solubilities of examples and reference compounds are listed below in Table 3.

TABLE 3

| Compound | Aqueous solubility pH 7.4 (µM) (±standard deviation), shake-flask method |
| --- | --- |
| Compound A | 72.4 (±2.6) |
| Compound B | 17.7 (±2.7) |
| Example 3 | 188 (±6.0) |
| Example 4 | 114 (±3.0) |

PAMPA Permeability Assay

Artificial membrane permeability was determined as follows: Tested compounds were dissolved to 10 mM in 100% DMSO. Permeability of compounds was measured in PBS (pH 7.4), 5% DMSO at 23° C. Safire (Tecan) plate reader was used for measurement the UV/Vis absorption. Protocol: Dilute stocks of tested compounds and controls with PBS to 1.67 mM and mix well by pipetting, add 280 µl of PBS, 5% DMSO to acceptor plate, add 5 µl of 2% L-α-Phosphatidylcholine suspension in dodecane to the membrane of donor plate. Immediately add 98 µl of PBS to donor plate and make the sandwich with acceptor plate. Add 42 µl of tested compounds and controls dilutions to acceptor plate, cover the plate, place into camera and incubate for 16 hours. Make the equilibrium plate, add 225 µl of PBS, 3.7% DMSO and 25 µl of tested compounds and controls dilutions to UV plate. After 16 hours pull the donor plate out and transfer 250 µl from acceptor plate to UV plate. Scan UV plate on Safire (Tecan) plate reader from 245 to 450 nM with step 5 nM. Permeability is reported in % of compound found in the receiver compartment after the incubation period. Applying this protocol, PAMPA permeabilities of examples and reference compounds were determined as follows (see Table 4):

TABLE 4

| Compound | PAMPA Permeability |
| --- | --- |
| Compound A | 32% |
| Compound B | 7% |
| Example 1 | 54% |
| Example 2 | 43% |

Plasma Protein Binding Assay

Plasma protein binding was determined using the filtration method:

Preparation of standards: working solutions were prepared for each calibration level by appropriate dilution of the corresponding stock solution. Calibration standards were prepared by spiking 147 µl PBS buffer with 3 µl of the corresponding working solution. Sample preparation: The sample and standard solution preparation was performed by mixing equal volumes of acetonitrile containing the internal standard (1 µM) with 75 µl sample, or 150 µl calibration standard solution, respectively. After vigorously shaking the samples were centrifuged (6000 g) for 5 minutes. Aliquots of the supernatants were subjected to LC-MS/MS analysis. Assay procedure: Compound stock solutions were diluted in acetonitrile to give a 50-fold concentrated working solution. The incubation solutions were prepared by adding 3 µl of a 50-fold concentrated working solution in acetonitrile to 147 µl of lithium-heparin plasma from mice giving an incubation concentration of 1 µM. Recovery samples were prepared analogously with mouse plasma filtrate (MF) instead of the corresponding plasma to consider the method recovery (matrix and filter device) of the test compound. The test and recovery solutions were incubated at 37° C. for one hour and subsequently centrifuged at 6500 g for 12 minutes using centrifugal filter units. Aliquots of the filtrate and plasma filtrates were processed for acetonitrile precipitation. The percentage of compound bound to plasma proteins (% PPB) was calculated using the following equation:

PPB[%]=100−(concentration$_{compound\ plasma\ filtrate}$/mean concentration$_{compound\ filtrated\ plasma\ filtrate}$)×100.

Applying this protocol, plasmaprotein binding of examples and reference compounds was determined as listed below in Table 5.

TABLE 5

| Compound | Plasma protein binding (%) (±standard deviation) |
|---|---|
| Compound A | 99.3 (±0.12) |
| Example 3 | 97.9 (±0.07) |

Microsomal Stability Assay

In vitro assays were performed to evaluate the metabolic stability of test items in liver microsomes originating from mouse. Preparation of working standards of test items: Working solutions were prepared for each calibration level by appropriate dilution of the corresponding stock solution, depending on each compound's solubility in acetonitrile or acetonitrile/water. Calibration standards were prepared by spiking 196 µl standard matrix with 4 µl of the corresponding working solution. The standard matrix consists of 0.15 mg/ml of microsomal protein in phosphate buffer (100 mM pH 7.4), the final standard solutions contain 2% acetonitrile. The samples and standard solutions were extracted with ethyl acetate, isolation of the compounds was performed by addition of 600 µl ethyl acetate containing the internal standard (0.1 µM) to 200 µl sample and calibration standard. After vigorously shaking (10 minutes) and centrifugation (5000 g) the aqueous phase was separated by freezing in an acetone/dry ice bath and the organic phase is evaporated to dryness using a vacuum centrifuge. Samples were reconstituted in 200 µl acetonitrile/water mix (1:1 v/v) and subsequently subjected to LC-MS/MS. The incubation solution (180 µl) consisted of 90 µl of a microsomal suspension of 0.33 mg/ml of protein in phosphate buffer 100 mM pH 7.4 and 90 µl NADP-regenerating system. The reaction was initiated by the addition of 20 µl of test compound (in 20% acetonitrile) to the preincubated microsomes/buffer mix at 37° C. 200 µl samples were removed from the incubation after 0, 5, 10, and 30 minutes and processed for ethyl acetate extraction as described above. Negative controls using boiled microsomes (boiling water bath, 25 minutes) without regenerating system were run in parallel. The amount of compound in the samples is expressed as percentage of remaining compound compared to time point zero (=100%). These percentages were plotted against the corresponding time points. Intrinsic clearance ($CL_{int}$) and half-life ($t_{1/2}$) estimates were determined using the rate of parent disappearance and following formula (1) and (2). (1) $CL_{int}$=(−k)×V×fu. (2) $t_{1/2}$=ln 2/−k. Where $C_{Lint}$=intrinsic clearance [µl/min/mg protein], $t_{1/2}$=half life [min], k=slope from the linear regression of log [test compound] versus time plot [1/min]. V=6666.7; fu=unbound fraction in the blood. Applying this protocol gave microsomal stabilities for examples and reference compounds as listed below in Table 6:

TABLE 6

| Compound | $t_{1/2}$(min) | $CL_{int}$ (µl/min/mg protein) |
|---|---|---|
| Compound A | 22 | 207 |
| Example 3 | 30 | 153 |
| Example 4 | 30 | 153 |

Determination of Pharmacokinetic Parameters in Mice

Data on the rate and extent of absorption of the test compounds were generated. Compounds were applied perorally at 5 mg/kg each to male 8 weeks old C57BL/6 mice and plasma concentrations of the test items were determined by LC-MS/MS. A solution of 2.5 mg/ml of each test item was produced by diluting them in the vehicle, 10% HPBCD (hydroxypropyl-beta-cyclodextrin) in 20 mM phosphate buffer pH 7.0 (v/w). These solutions were stirred overnight at room temperature and heated to 60° C. for 10 minutes, resulting in a full solubilization. Then, an identical volume of each solution were mixed together to constitute the cassette. The application was performed by administrating the solution perorally to the mice, with an application volume of 10 ml/kg. For each time point three mice were used, which showed during and after application normal behaviour. Blood samples were obtained by sacrificing three animals for each time point (10, 30, 60, 120, 240, and 480 min) followed by cardiac puncture. Blood samples were treated with Li-heparin during collection procedure and stored on ice until centrifugation at 645 g (5 min, 4° C.). Plasma was harvested and kept at −20° C. until being assayed. To 50 µl of mouse plasma sample 6 µl acetonitrile containing an internal standard was added. Samples were vigorously shaken and centrifuged for 10 minutes at 6000 g and 20° C. An aliquot of the particle-free supernatant was transferred to 200 µl sampler vials and subsequently subjected to LC MS/MS for quantification. Plasma concentrations measured for timepoints are given in Table 7 below.

TABLE 7

| Compound | sampling time [min] | mean plasma conc. [ng/ml] | standard deviation [ng/ml] |
|---|---|---|---|
| Compound A | 10 | 120 | 71 |
|  | 30 | 102 | 73 |
|  | 60 | 43 | 43 |
|  | 120 | 24 | 13 |
|  | 240 | 15 | 6 |
|  | 480 | 8 | 3 |
| Example 3 | 10 | 904 | 277 |
|  | 30 | 867 | 504 |
|  | 60 | 291 | 342 |
|  | 120 | 214 | 68 |
|  | 240 | 63 | 5 |
|  | 480 | 20 | 12 |

Concentrations were plotted against sampling time for illustrating higher plasma levels of example 3 compared to plasma levels of compound A. The results are illustrated in FIG. 1.

PK calculation: The pharmacokinetic analysis of raw data was performed by applying a non-compartment model using the PK Solutions 2.0 software (Summit Research Services, Montrose, USA). All given parameters are model independent and were obtained by trapezoid area calculation and have the following meaning:

$C_{max\,obs}$: maximal measured concentration;

$t_{max\,obs}$: time to reach the maximum measured concentration;

$AUC_{0-\infty}$: area under the concentration-time curve extrapolated to infinity;

Vd: volume of distribution during elimination phase;

CL: total body clearance.

Pharmacokinetic parameters were computed for compounds A and example 3 as given in Table 8 below indicating a higher peak plasma level, a higher oral bioavailability and a lower clearance for example 3 compared to compound A.

TABLE 8

|  | Compound A | Example 3 |
| --- | --- | --- |
| Dose route | po | po |
| Dosage (mg/kg) | 5 | 5 |
| $C_{max\,obs}$ (ng/ml) | 119.6 | 903.9 |
| $t_{max\,obs}$ (min) | 10 | 10 |
| $AUC_{0-\infty}$ (ng*min/ml) | 14544 | 84507 |
| Vd (ml/kg) | 110078 | 9271 |
| CL (ml/(min*kg)) | 343 | 59 |

The invention claimed is:

1. A compound of formula (I)

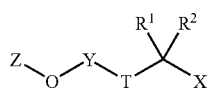

(I)

or an enantiomer, diastereomer, tautomer, or pharmaceutically acceptable salt thereof, wherein $R^1$ and $R^2$ are independently from each other selected from hydrogen, fluorine, cyano, nitro, azido, $NR^5R^6$, $OR^5$, $SR^5$, $C_1$-$C_6$ alkyl, $C_2$-$C_6$ alkenyl, $C_2$-$C_6$ alkynyl, $C_3$-$C_6$ cycloalkyl; or $R^1$ and $R^2$ are together =S; or $R^1$ and $R^2$ may together form a 3-6-membered carbocyclic or heterocyclic ring which each can be unsaturated or saturated, wherein each alkyl, alkenyl, alkynyl, cycloalkyl group, carbocyclic or heterocyclic ring is unsubstituted or substituted with one to five substituents $R^{11}$;

$R^5$ and $R^6$ are independently from each other selected from hydrogen, $C_1$-$C_6$-alkyl and $C_3$-$C_6$-cycloalkyl; or $R^5$ and $R^6$ together may form a 3-6-membered saturated heterocyclic ring, wherein the alkyl, cycloalkyl and heterocyclic group is unsubstituted or substituted with one to five substituents $R^{11}$;

X is

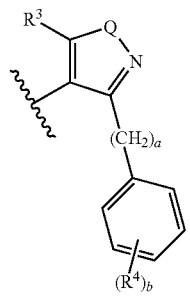

$R^3$ is hydrogen, halogen, cyano, nitro, azido, $C_1$-$C_6$ alkyl, $C_2$-$C_6$ alkenyl, $C_2$-$C_6$ alkynyl, $C_3$-$C_6$ cycloalkyl, heterocyclyl, aryl, heteroaryl, —$NR^{19}R^{20}$, $NR^{19}S(O)_mR^{20}$, $NR^{19}C(O)OR^{20}$, $NR^{19}C(O)R^{20}$, $NR^{19}C(O)NR^{19}R^{20}$, $OR^{19}$, $OC(O)R^{19}$, $S(O)_iR^{19}$, $SO_2NR^{19}C(O)R^{20}$, $S(O)_mNR^{19}R^{20}$, $C(O)R^{19}$, $C(O)OR^{20}$, $C(O)NR^{19}R^{20}$, $C(NR^{19})NR^{19}R^{20}$, wherein each alkyl, alkenyl, alkynyl, cycloalkyl heterocyclyl, aryl or heteroaryl is unsubstituted or substituted with one to five substituents $R^{11}$;

$R^{19}$ and $R^{20}$ are independently from each other selected from hydrogen, $C_1$-$C_6$-alkyl, $C_2$-$C_6$-alkenyl, $C_2$-$C_6$ alkynyl and $C_3$-$C_6$-cycloalkyl, or $R^{19}$ and $R^{20}$ together may form a 3-7-membered heterocyclic or heteroaromatic ring, wherein the $C_1$-$C_6$-alkyl, $C_2$-$C_6$-alkenyl, $C_3$-$C_6$-cycloalkyl, heterocyclyl and heteroaryl group is unsubstituted or substituted with one to five substituents $R^{11}$;

$R^4$ is independently selected from hydrogen, halogen, cyano, nitro, azido, $C_1$-$C_6$ alkyl, $C_2$-$C_6$ alkenyl, $C_2$-$C_6$ alkynyl, $C_3$-$C_6$ cycloalkyl, heterocyclyl, aryl, heteroaryl, $NR^{15}R^{16}$, $NR^{15}SO_2R^{16}$, $NR^{15}C(O)OR^{16}$, $NR^{15}C(O)R^{16}$, $NR^{15}C(O)NR^{15}R^{16}$, $NR^{15}C(NCN)NR^{15}R^{16}$, $OR^{15}$, $OC(O)R^{15}$, $S(O)_iR^{15}$, $SO_2NR^{15}C(O)R^{16}$, $S(O)_mNR^{15}R^{16}$, $SC(O)R^{15}$, $C(O)R^{15}$, $C(O)OR^{15}$, $C(O)NR^{15}R^{16}$, $C(O)NHOR^{15}$, $C(O)SR^{15}$ and $C(NR^{15})NR^{15}R^{16}$, wherein each alkyl, alkenyl, alkynyl, cycloalkyl, heterocyclyl, aryl or heteroaryl is unsubstituted or substituted with one to five substituents $R^{11}$;

and further two substituents $R^4$ can be taken together with the atom to which they attach to form a 4-7 membered carbocyclic, aryl, heteroaryl or heterocyclic ring, each of which is substituted or unsubstituted with one to five substituents $R^{11}$;

$R^{15}$ and $R^{16}$ are independently from each other selected from hydrogen, $C_1$-$C_6$-alkyl, $C_2$-$C_6$-alkenyl, $C_2$-$C_6$ alkynyl and $C_3$-$C_6$-cycloalkyl; or $R^{15}$ and $R^{16}$ together may form a 3-7-membered heterocyclic or heteroaromatic ring, wherein the alkyl, alkenyl, cycloalkyl, heterocyclyl and heteroaryl groups are unsubstituted or substituted with one to five substituents $R^{11}$;

$R^{11}$ is independently selected from hydrogen, halogen, cyano, nitro, azido, =O, =S, $C_1$-$C_6$ alkyl, $C_2$-$C_6$ alkenyl, $C_2$-$C_6$ alkynyl, $C_3$-$C_6$ cycloalkyl, heterocyclyl, aryl, heteroaryl, $NR^{12}R^{13}$, $NR^{12}S(O)_mR^{13}$, $NR^{12}C(O)OR^{13}$, $NR^{12}C(O)R^{13}$, $NR^{12}C(O)NR^{12}R^{13}$, $NR^{12}C(NCN)NR^{12}R^{13}$, =$NOR^{12}$, —$OR^{12}$, $OC(O)R^{12}$, $S(O)_iR^{12}$, $SO_2NR^{12}C(O)R^{13}$, $S(O)_mNR^{12}R^{13}$, $SC(O)R^{12}$, $C(O)R^{12}$, $C(O)OR^{12}$, $C(O)SR^{12}$, $C(O)NR^{12}R^{13}$, $C(O)NOR^{12}$, and $C(NR^{12})NR^{12}R^{13}$;

$R^{12}$ and $R^{13}$ are independently from each other selected from hydrogen, $C_1$-$C_6$ alkyl and $C_3$-$C_6$ cycloalkyl, wherein each alkyl or cycloalkyl may be unsubstituted or substituted with one to five fluorines and/or one or two substituents selected from OH, OCH$_3$, OCH$_2$F, OCHF$_2$, OCF$_3$, =O, SCF$_3$, NH$_2$, NHCH$_3$ and N(CH$_3$)$_2$; or R$^{12}$ and R$^{13}$ can be taken together with the atom to which they are attached to form a 4 to 6 membered carbocyclic, heteroaryl or heterocyclic ring, each of which may be unsubstituted or substituted with one to five fluorines and/or one or two substituents selected from OH, OCH$_3$, —OCH$_2$F, OCHF$_2$, OCF$_3$, =O, SCF$_3$, NH$_2$, NHCH$_3$ and N(CH$_3$)$_2$;

Q is O;

T is —O—, —S—, —N(R$^{14}$)—, CH$_2$ or CF$_2$;

R$^{14}$ is hydrogen, C$_1$-C$_3$-alkyl or C$_3$-C$_5$ cycloalkyl, wherein each alkyl or cycloalkyl is unsubstituted or substituted with 1-5 fluorine atoms;

Y is selected from

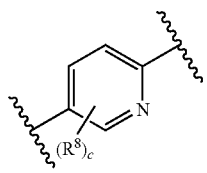 (Y$^1$)

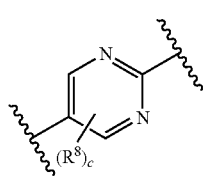 (Y$^2$)

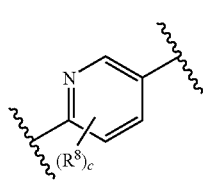 (Y$^3$)

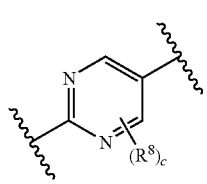 (Y$^4$)

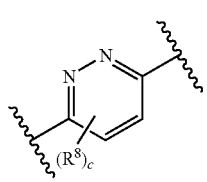 (Y$^5$)

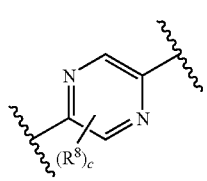 (Y$^6$)

R$^8$ is independently selected from hydrogen, halogen, cyano, nitro, azido, C$_1$-C$_6$ alkyl, C$_2$-C$_6$ alkenyl, C$_2$-C$_6$ alkynyl, C$_3$-C$_6$ cycloalkyl, heterocyclyl, aryl, heteroaryl, NR$^{12}$R$^{13}$, NR$^{12}$S(O)$_m$R$^{13}$, NR$^{12}$C(O)OR$^{13}$, NR$^{12}$C(O)R$^{13}$, NR$^{12}$C(O)NR$^{12}$R$^{13}$, OR$^{12}$, OC(O)R$^{12}$, S(O)$_i$R$^{12}$, SO$_2$NR$^{12}$C(O)R$^{13}$, S(O)$_m$NR$^{12}$R$^{13}$, C(O)R$^{12}$, C(O)OR$^{12}$, C(O)NR$^{12}$R$^{13}$, and C(NR$^{12}$)NR$^{12}$R$^{13}$, wherein each alkyl, alkenyl, alkynyl, cycloalkyl, heterocyclyl, aryl or heteroaryl is unsubstituted or substituted with one to five substituents R$^{11}$;

Z is phenyl-A-R$^9$, pyridyl-A-R$^9$, pyrimidyl-A-R$^9$ or pyridazyl-A-R$^9$, wherein phenyl, pyridyl, pyrimidyl or pyridazyl is unsubstituted or substituted with one to three groups selected from halogen, C$_1$-C$_4$ alkyl, C$_3$-C$_5$ cycloalkyl, C$_2$-C$_4$ alkenyl, C$_2$-C$_4$ alkynyl, cyano, OH, OCH$_3$, OCH$_2$F, OCHF$_2$, OCF$_3$, SCF$_3$, NH$_2$, NHCH$_3$ and N(CH$_3$)$_2$;

A is a bond, CH$_2$, CHCH$_3$, C(CH$_3$)$_2$ or CF$_2$;

R$^9$ is hydrogen, COOR$^{17}$, CONR$^{17}$R$^{18}$, C(O)NHSO$_2$R$^{17}$, SO$_2$NHC(O)R$^{17}$, S(O)$_m$R$^{17}$, or tetrazole which is connected to A via the C-atom;

R$^{17}$ and R$^{18}$ are independently from each other selected from hydrogen, C$_1$-C$_6$-alkyl, C$_2$-C$_6$-alkenyl, C$_2$-C$_6$ alkynyl and C$_3$-C$_6$-cycloalkyl; or R$^{17}$ and R$^{18}$ together may form a 3-7-membered heterocyclic or heteroaromatic ring, wherein the C$_1$-C$_6$-alkyl, C$_2$-C$_6$-alkenyl, C$_3$-C$_6$-cycloalkyl, heterocyclyl and heteroaryl groups are unsubstituted or substituted with one to five substituents R$^{11}$;

a is 0 or 1;
b is 1, 2 or 3;
c is 1 or 2;
i is 0, 1 or 2; and
m is 1 or 2.

2. The compound according to claim 1, wherein
R$^1$ and R$^2$ are independently selected from hydrogen, fluorine and C$_{1-6}$ alkyl, wherein the alkyl group is unsubstituted or substituted with one to five substituents R$^{11}$; or R$^1$ and R$^2$ are together =S.

3. The compound according to claim 1, wherein
R$^3$ is hydrogen, C$_1$-C$_6$ alkyl, NR$^{19}$R$^{20}$ or C$_3$-C$_6$ cycloalkyl, wherein each alkyl or cycloalkyl is unsubstituted or substituted with one to five substituents R$^{11}$.

4. The compound according to claim 1, wherein
R$^4$ is hydrogen, halogen, C$_{1-6}$ alkyl, O—C$_1$-C$_6$ alkyl or CN, wherein each alkyl group is unsubstituted or substituted by one to five substituents R$^{11}$.

5. The compound according to claim 1, wherein
T is O, CH$_2$ or NR$^{14}$.

6. The compound according to claim 1, wherein
Y is selected from formula (Y$^1$), (Y$^3$) and (Y$^5$).

7. The compound according to claim 1, wherein
R$^8$ is hydrogen, halogen, C$_1$-C$_6$-alkyl or O—C$_1$-C$_3$-alkyl, wherein each alkyl group is unsubstituted or substituted with one to five substituents R$^{11}$.

8. The compound according to claim 1, wherein
Z is phenyl-A-R$^9$, wherein phenyl is unsubstituted or substituted with one to three groups selected from halogen, cyano, C$_{1-4}$ alkyl, OH, OCH$_3$, OCH$_2$F, OCHF$_2$, OCF$_3$, SCF$_3$, NH$_2$, NHCH$_3$ and N(CH$_3$)$_2$.

9. The compound according to claim 1, wherein
R$^9$ is COOR$^{17}$ or CONR$^{17}$R$^{18}$.

10. A medicament comprising the compound according to claim 1.

11. A pharmaceutical composition comprising at least one compound according to claim 1 and at least one pharmaceutically acceptable excipient and/or carrier.

12. A method for the treatment of a disease or condition mediated by FXR comprising administering a composition comprising the compound of claim 1.

13. The method according to claim 12, wherein said disease or condition involves chronic intrahepatic or forms of extrahepatic cholestatic conditions, or liver fibrosis resulting from chronic cholestatic conditions or acute intraheptic cholestatic conditions.

14. The method according to claim 13, wherein the chronic intraheptic or cholestatic conditions are primary biliary cirrhosis (PBC), primary sclerosing cholangitis (PSC), progressive familiar cholestasis (PFIC), alcohol-induced cirrhosis and associated cholestasis, or the liver fibrosis is estrogen or drug induced cholestasis.

15. The method according to claim 12, wherein said disease or condition involves obstructive or chronic inflammatory disorders that arise out of improper bile composition.

16. The method according to claim 15, wherein the obstructive or chronic inflammatory disorders are cholelithiasis (cholesterol gallstones).

17. The method according to claim 12, wherein said disease or condition involves gastrointestinal conditions with a reduced uptake of dietary fat and fat-soluble dietary vitamins.

18. The method according to claim 12, wherein said disease or condition is Inflammatory Bowel Diseases.

19. The method according to claim 18, wherein the inflammatory bowel diseases are Crohn's disease or Colitis Ulcerosa.

20. The method according to claim 12, wherein said disease or condition involves lipid and lipoprotein disorders.

21. The method according to claim 20, wherein the lipid and lipoprotein disorders are hypercholesterolemia, hypertriglyceridemia, or atherosclerosis as a clinically manifest condition.

22. The method according to claim 12, wherein said disease or condition is Type II Diabetes.

23. The method according to claim 12, wherein said disease or condition involves clinical complications of Type I and Type II Diabetes.

24. The method according to claim 23, wherein the clinical complications of Type I and Type II Diabetes are Diabetic Nephropathy, Diabetic Retinopathy, Diabetic Neuropathies or Peripheral Arterial Occlusive Disease (PAOD).

25. The method according to claim 12, wherein said disease or condition is for conditions and diseases which result from chronic fatty and fibrotic degeneration of organs due to enforced lipid and specifically triglyceride accumulation and subsequent activation of profibrotic pathways.

26. The method according to claim 25, wherein the conditions and diseases are Non-Alcoholic Steatohepatitis (NASH) and chronic cholestatic conditions in the liver, Glomerulosclerosis and Diabetic Nephropathy in the kidney, Macula Degeneration and Diabetic Retinopathy in the eye and Neurodegenerative diseases in the brain or Diabetic Neuropathies in the peripheral nervous system.

27. The method according to claim 12, wherein said disease or condition is obesity and metabolic syndrome (combined conditions of dyslipidemia, diabetes and abnormally high body-mass index).

28. The method according to claim 12, wherein said disease or condition is acute myocardial infarction, acute stroke, or thrombosis which occur as an endpoint of chronic obstructive atherosclerosis.

29. The method according to claim 12, wherein said disease or condition is persistant infections by intracellular bacteria or parasitic protozoae.

30. The method according to claim 29, wherein the bacteriyl or parasitic protozoae are selected from *Mycobacterium* spec. (Treatment of Tuberculosis or Lepra), *Listeria monocytogenes* (Treatment of Listeriosis), *Leishmania* spec. (Leishmaniosis), *Trypanosoma* spec. (Chagas Disease; Trypanosomiasis; Sleeping Sickness).

31. The method according to claim 12, wherein said disease or condition is non-malignant hyperproliferative disorders.

32. The method according to claim 31, wherein the non-malignant hyperproliferative disorders are increased neointima formation after balloon vessel dilatation and stent application due to increased proliferation of vascular smooth muscle cells (VSMCs) Bening Prostate Hyperplasia (BPH), or other forms of scar tissue formation and fibrotisation.

33. The method according to claim 12, wherein said disease or condition involves malignant hyperproliferative disorders.

34. The method according to claim 33, wherein the malignant hyperproliferative disorders are cancer.

35. The method according to claim 12, wherein said disease or condition is liver steatosis and associated syndromes, cholestatic and fibrotic effects that are associated with alcohol-induced cirrhosis or with viral-borne forms of hepatitis.

36. The method according to claim 35, wherein the liver steatosis associated syndrome is non-alcoholic steatohepatitis ("NASH").

37. A method for preparing the compound of formula (I) according to claim 1 comprising the step of reacting a compound of formula (IXa) or of formula (IXb)

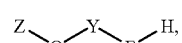
(IXa)

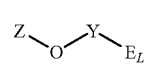
(IXb)

wherein
$E_N$-H is OH, SH, $NH_2$, $N(R^{14})H$, NH(CO)O-alkyl, NH(CO)O-aryl, $NH(SO)_2$aryl, $NH(SO)_2$alkyl, $CH_3$ or $CF_2H$;
$E_L$ is halogen, OH, OC(O)alkyl, OC(O)aryl, O-aryl, O-pentafluorophenyl, O-sulfonylalkyl, O-sulfonylaryl, O-succinylimido, O-benzotriazolyl, nitro, azido, S-alkyl, $SO_2$alkyl, $SO_2$aryl, SC(O)alkyl, SC(O)aryl or cyano;
with a compound of formula (IVa) or (IVb), respectively

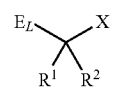
(IVa)

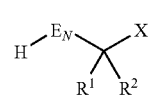
(IVb)

wherein
$R^1$, $R^2$ and X are as defined previously and
$E_L$ and $E_N$-H are as defined above;
in order to obtain a compound of formula (I)

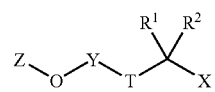
(I)

wherein Z, Y, T, $R^1$, $R^2$ and X are as defined previously.

38. The method according to claim 37, comprising the further step of reacting a compound of formula (XII)

Z-L$_A$    (XII)

wherein
Z is as defined previously and
L$_A$ is halogen, OH, B(OH)$_2$, B(OMe)$_2$, BF$_3^-$ or 4,4,5,5-tetramethyl-1,3,2-dioxaborolan-2-yl;
with a compound of formula (XIII)

    (XIII)

wherein
Y is as defined previously,
L$_B$ is halogen, OH, B(OH)$_2$, B(OMe)$_2$, BF$_3^-$ or 4,4,5,5-tetramethyl-1,3,2-dioxaborolan-2-yl and E is E$_L$ or E$_N$-H;
in order to obtain a compound of formula (IX)

    (XIV)

39. The method according to claim 37, wherein
Z is as defined previously,
Y is Y$^1$, Y$^3$ or Y$^5$,
T is O,
R$^1$ and R$^2$ are hydrogen and
a is 0.

40. The compound according to claim 1, wherein Y is Y$^1$ or Y$^3$.

* * * * *